United States Patent
Wampler et al.

(10) Patent No.: US 6,676,660 B2
(45) Date of Patent: Jan. 13, 2004

(54) FEEDBACK LIGHT APPARATUS AND METHOD FOR USE WITH AN ELECTROSURGICAL INSTRUMENT

(75) Inventors: Scott D. Wampler, West Chester, OH (US); David C. Yates, West Chester, OH (US); Trevor W. V. Speeg, Williamsburg, OH (US); Jeffrey J. Vaitekunas, West Chester, OH (US); Vance V. Van Drake, III, Lubbock, TX (US); Ryan Niezgoda, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 101 days.

(21) Appl. No.: 10/055,782

(22) Filed: Jan. 23, 2002

(65) Prior Publication Data

US 2003/0139742 A1 Jul. 24, 2003

(51) Int. Cl.⁷ .............................................. A61B 18/18
(52) U.S. Cl. ............................ 606/51; 606/38; 606/50
(58) Field of Search ..................... 606/32, 34, 37–41, 606/49–52

(56) References Cited

U.S. PATENT DOCUMENTS

| | | |
|---|---|---|
| 2,002,594 A | 5/1935 | Wappler et al. |
| 2,041,682 A | 5/1936 | Adrian |
| 3,875,945 A * | 4/1975 | Friedman ..................... 606/45 |
| 4,597,379 A | 7/1986 | Kihn et al. |
| 4,800,878 A | 1/1989 | Cartmell |
| 4,848,335 A | 7/1989 | Manes |
| 5,404,412 A | 4/1995 | Seino et al. |
| 5,442,459 A | 8/1995 | Gahang |
| 5,445,648 A | 8/1995 | Cook |
| 5,458,598 A | 10/1995 | Feinberg et al. |
| 5,574,545 A | 11/1996 | Hosoi et al. |
| 5,599,350 A | 2/1997 | Schulze et al. |
| 5,700,261 A | 12/1997 | Brinkerhoff |
| 5,707,469 A | 1/1998 | Hixson et al. |
| 5,745,849 A | 4/1998 | Britton |
| 5,762,609 A | 6/1998 | Benaron et al. |
| 5,766,166 A | 6/1998 | Hooven |
| 5,797,948 A | 8/1998 | Dunham |
| 5,800,449 A | 9/1998 | Wales |
| 5,817,091 A * | 10/1998 | Nardella et al. .............. 606/38 |
| 5,947,964 A | 9/1999 | Eggers et al. |
| 5,951,549 A | 9/1999 | Richardson et al. |
| 6,010,516 A | 1/2000 | Hulka |
| 6,033,399 A | 3/2000 | Gines |
| 6,086,586 A | 7/2000 | Hooven |
| 6,106,524 A | 8/2000 | Eggers et al. |
| 6,132,429 A | 10/2000 | Baker |
| 6,183,468 B1 | 2/2001 | Swanson et al. |

(List continued on next page.)

FOREIGN PATENT DOCUMENTS

| | | |
|---|---|---|
| WO | 99/12488 A1 | 3/1999 |
| WO | 00/24330 A1 | 5/2000 |
| WO | 00/24440 A1 | 5/2000 |
| WO | 00/47124 A1 | 8/2000 |
| WO | WO 01/80757 A | 11/2001 |

Primary Examiner—Michael Peffley
(74) Attorney, Agent, or Firm—Verne E. Kreger, Jr.

(57) ABSTRACT

The present invention relates, in general, to electrosurgical instruments and, more particularly, to a feedback light used in cooperation with an electrosurgical instrument. The present invention further comprises first and second moveable jaws. A first electrode is housed within the first moveable jaw and a second electrode is housed within the second moveable jaw, where the electrodes are connectable to a power source for providing an electric current between the electrodes. The present invention further comprises a feedback light connectable to a first lead and a second lead in order to form a second circuit, where the second circuit is adjacent to the first circuit in order to facilitate capacitive coupling between the first and second circuits in order to light a feedback light.

12 Claims, 30 Drawing Sheets

U.S. PATENT DOCUMENTS

| | | |
|---|---|---|
| 6,245,065 B1 | 6/2001 | Panescu et al. |
| 6,258,085 B1 | 7/2001 | Eggleston |
| 6,296,640 B1 | 10/2001 | Wampler et al. |
| 6,334,861 B1 | 1/2002 | Chandler et al. |
| 2002/0002372 A1 * | 1/2002 | Jahns et al. .................. 606/41 |
| 2002/0107517 A1 | 8/2002 | Faller |

* cited by examiner

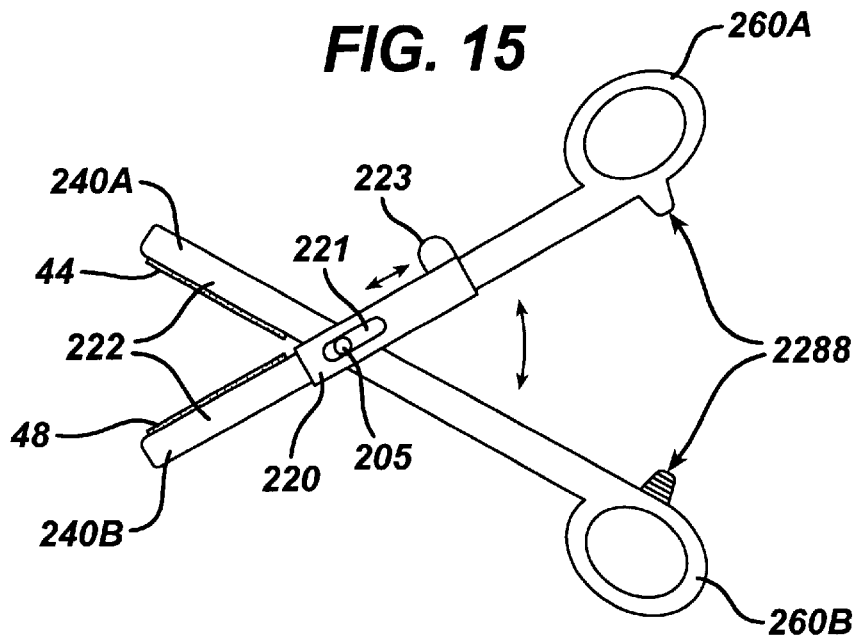
FIG. 15
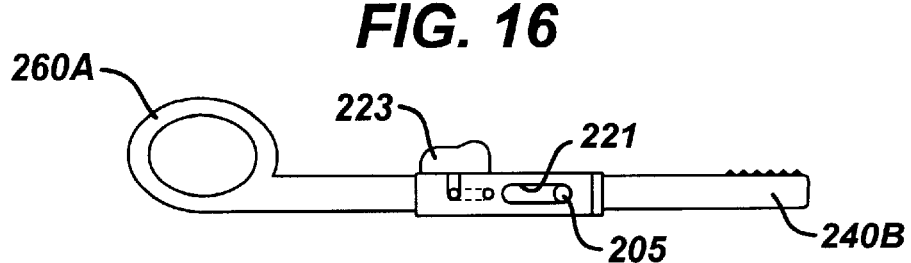
FIG. 16

FIG. 19
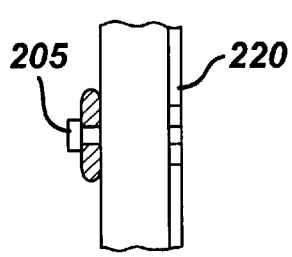 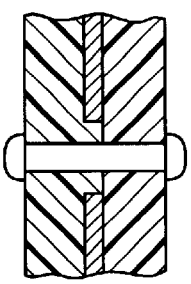
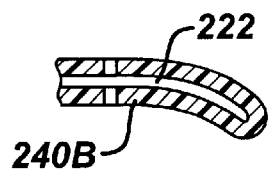
FIG. 20

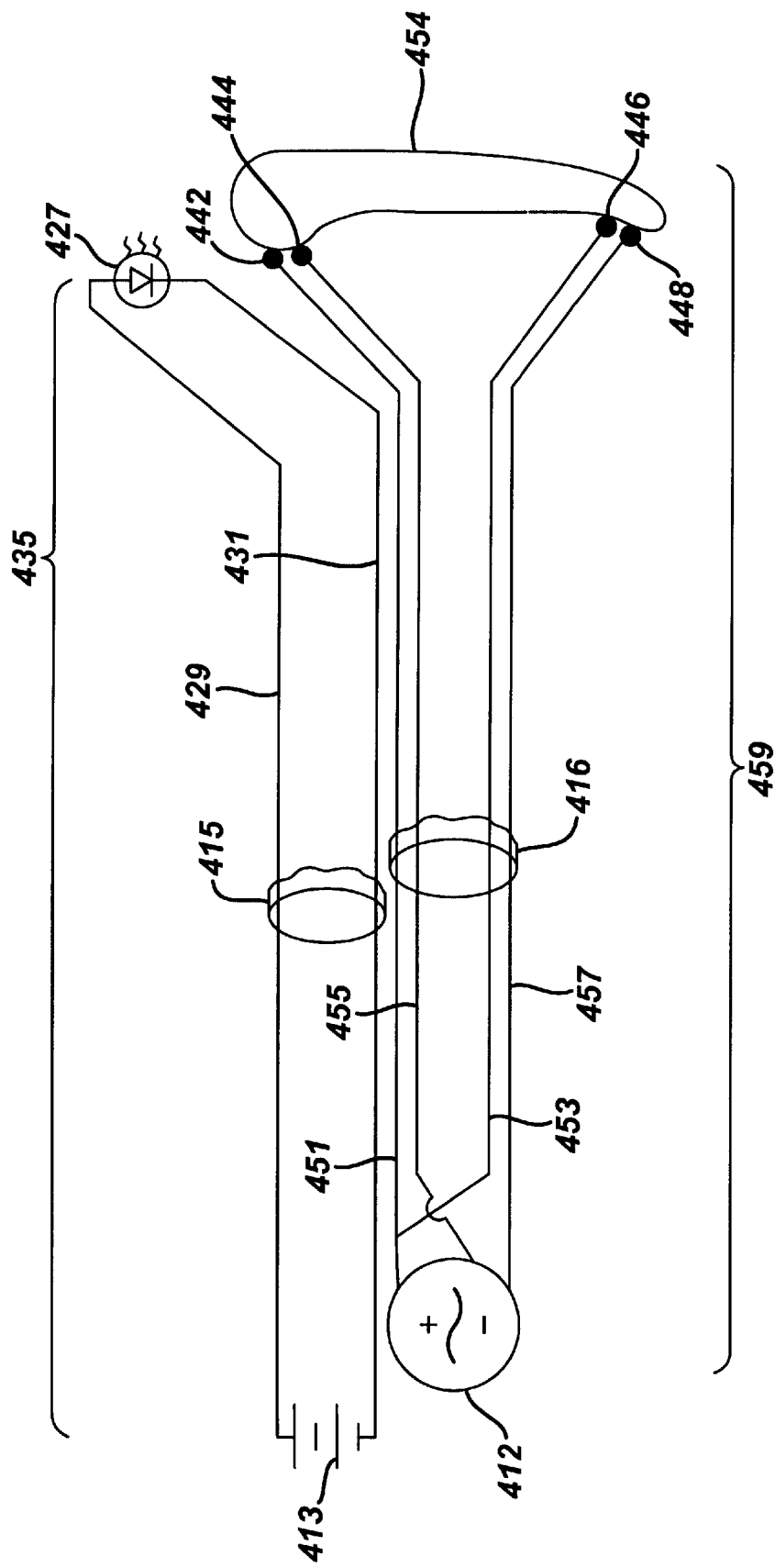

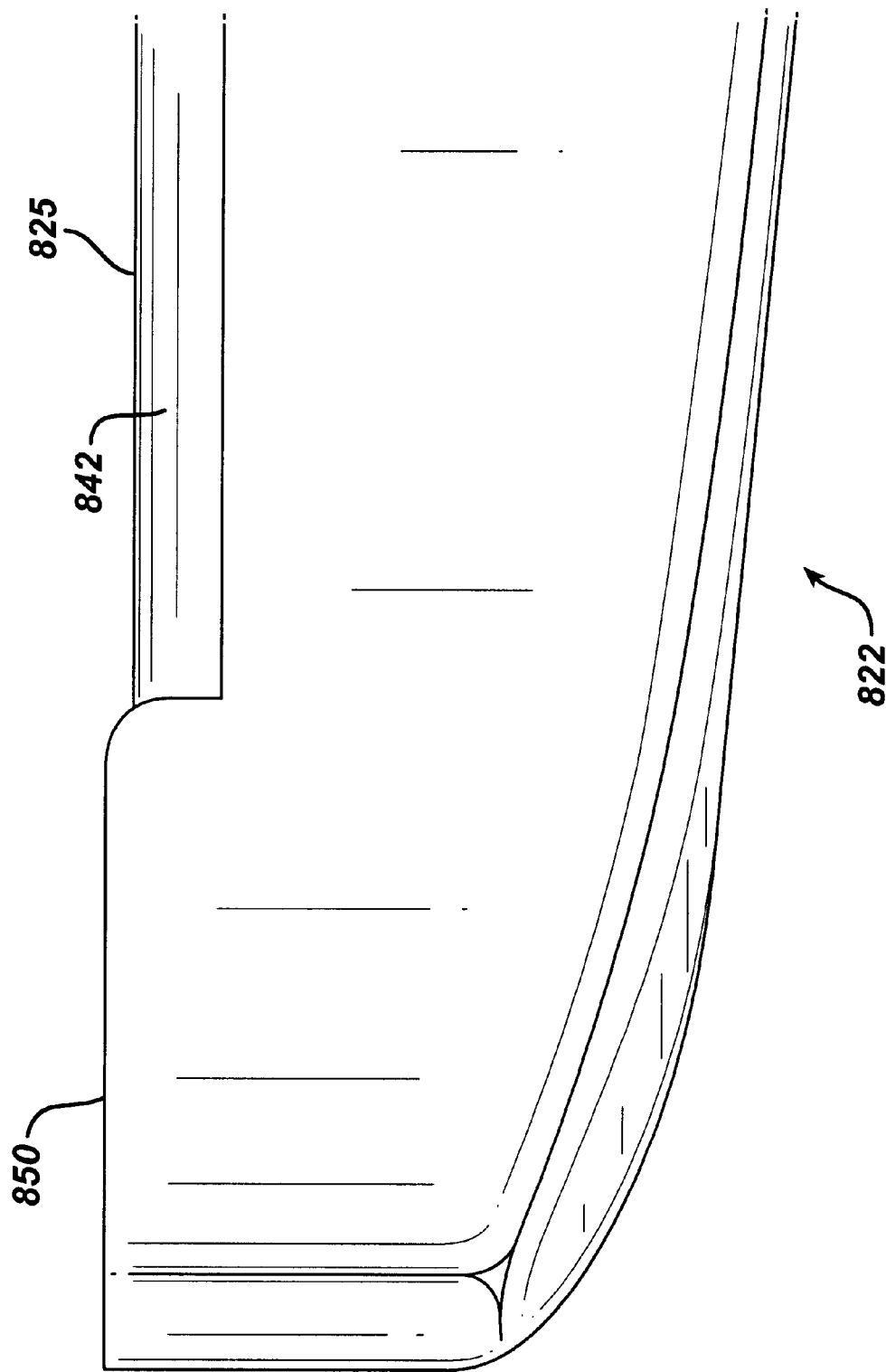

FEEDBACK LIGHT APPARATUS AND METHOD FOR USE WITH AN ELECTROSURGICAL INSTRUMENT

FIELD OF THE INVENTION

The present invention relates, in general, to electrosurgical instruments and, more particularly, to a feedback light apparatus and method used in cooperation with an electrosurgical instrument.

BACKGROUND OF THE INVENTION

The application of heat to treat bleeding wounds dates back to antiquity, with a hot iron being widely applied in medieval times to cauterize battle wounds to stop bleeding. In cauterization, the essential mechanism behind the treatment is using conductive heat transfer from a hot object to raise the temperature of the bleeding tissue sufficiently high to denature the tissue proteins, or heat the blood sufficiently high to cause a thrombus to form.

Coagulation by means of electrosurgery is also accomplished by heating tissue, but the primary mechanism is electrical power dissipation in the affected tissue, rather than heat transfer from an external object. Current flows through the tissue, and is resisted by the tissue. This creates a small envelope of steam around the electrodes of the electrosurgical instrument, and the steam vaporizes the tissue to cause cellular dehydration, denaturation of proteins, and tissue shrinkage, leading to blood vessel thrombosis. This form of hemostasis is now routinely used in both open and endoscopic surgery for small blood vessels (typically smaller than 1 mm), and has largely replaced individual vessel ligation.

Currently-available bipolar grasping instruments for electro-coagulation of tissue, or "tissue welding," generally use only two electrodes of opposite polarity, one of which is located on each of the opposite jaws of the grasper. As illustrated in FIG. 1, in use, tissue is held between a pair of grasper jaws (shown in cross-section) having first and second electrodes (Electrode 1 and Electrode 2) of opposite polarity. Bipolar current flows between the two electrodes along the illustrated current flow lines, with tissue coagulating first at the edges of the jaws. Then, as the tissue dries out and the impedance increases, the current flows through the moister tissue and the coagulation spreads both inward toward the center of the jaws and outward from the jaw edges. The tissue coagulation and heating outside the jaw continues until the power is shut off.

Thermal damage to adjacent structures can occur due to this spread of thermal energy outside the jaws of the instrument. Because of the spread of thermal energy outside the jaws of the instrument, it is difficult to coagulate long sections of tissue, such as bowel, lung, or larger blood vessels, without significant lateral thermal spread. Over-coagulation frequently occurs, resulting in tissue sticking to the jaws of the instrument. When the jaws of the instrument are opened, if the tissue sticking is severe, the tissue can be pulled apart, thus adversely affecting hemostasis. Under-coagulation can occur if insufficient energy has been applied to the tissue, and the resulting hemostasis will be incomplete.

Some electrosurgical devices measure the impedance of tissue to be affected as a feedback parameter to maintain the impedance of the tissue within predetermined limits by controlling the level of electrosurgical energy. By controlling the level of electrosurgical energy applied to a tissue area, the electrosurgical device allows simultaneous cutting and cauterization of tissue independently of a user's technique.

Other electrosurgical tools have digital display units or bar graph displays for indicating power, voltage and other parameters relating to electrosurgical device operation. Such displays often provide a theoretical value and not a value measured at a relevant tissue area. While these displays might provide some information, actual measurements of the affected tissue are necessary in order to allow a user to most effectively cut and cauterize tissue during an electrosurgical procedure. Furthermore, such graphical displays require a user to focus attention on the display for an amount of time necessary to ascertain a display reading and process that information.

Still other electrosurgical devices provide an audible alarm that sounds when a theoretical energy level is exceeded, thus not providing information from an affected tissue area. Also, as one skilled in the art will appreciate, an audible alarm may be confused with other equipment having sounds associated therewith, such as cardiac and respiratory monitors.

U.S. Pat. No. 5,817,091 filed May 20, 1997 issued Oct. 6, 1998 to Medical Scientific, Inc. discloses an electrosurgical system having a visual indicator. The electrosurgical system further includes a lamp in electrical communication with the active and return electrodes, wherein the neon bulb is illuminated when the current flowing through the tissue exceeds a predetermined threshold.

U.S. Pat. No. 5,762,609 filed Jun. 7, 1995 issued Jun. 9, 1998 to Sextant Medical Corporation discloses a class of surgical tools constructed from the surgical tools and a tissue state monitoring device to assess or image changes in the chemical or structural composition of tissue over time.

U.S. Pat. No. 5,599,350 filed Apr. 3, 1995 issued Feb. 4, 1997 to Ethicon Endo-Surgery discloses an electrosurgical hemostatic instrument in which the coagulation status of tissue engaged by two elements delivering electrosurgical energy to tissue may be observed, and in which damage from thermal spread may be minimized.

U.S. Pat. No. 4,800,878 filed Aug. 26, 1987 issued Jan. 31, 1989 to Becton, Dickinson and Company discloses a disposable electrosurgical knife handle and blade with a built-in warning light positioned on the top of the handle in the surgeon's line of vision during surgical procedures in order to warn, instantly, of unwanted surges in the electrical system.

U.S. Pat. No. 6,258,085 filed May 11, 1999 issued Jul. 10, 2001 to Sherwood Services AG discloses a method of determining the probability of a patient burn under a return electrode in a monopolar electrode.

U.S. Pat. No. 6,245,065 filed Sep. 10, 1998 issued Jun. 12, 2001 to Scimed Life Systems, Inc. discloses systems and methods for controlling the power supplied to an electrosurgical probe. The systems and methods may be used to monitor electrode-tissue contact, adjust power in response to a loss of contact, and apply power.

Thus, it would be advantageous to provide an electrosurgical tissue welding instrument in which the current pathway is limited to tissue within the jaws, so as to minimize tissue damage due to thermal effects outside the jaws of the device. It would be advantageous to provide an electrosurgical tissue welding instrument which allows coagulation of a relatively long section of tissue, while minimizing the lateral spread of thermal energy. It would be advantageous to provide an electrosurgical tissue welding instrument in which the maximum current density in the coagulated tissue occurs away from the electrodes, and between two stick resistant surfaces, to minimize tissue sticking to the electrodes. It would be advantageous to provide an electrosurgical tissue welding instrument where the current flow is self-limiting to prevent over-coagulation of the tissue. It would be advantageous to provide an electrosurgical tissue welding instrument which provides a clear view of coagulated tissue to prevent under-coagulation of the tissue. It would be advantageous to provide an electrosurgical tissue welding instrument that provides a cutting capability combined with the other features and advantages described above.

SUMMARY OF THE INVENTION

The present invention relates, in general, to electrosurgical instruments and, more particularly, to a feedback light apparatus and method used in cooperation with an electrosurgical instrument. The present invention further comprises first and second moveable jaws each comprising a tissue contacting surface in face-to-face relating with the tissue contacting surface of the other jaw, where the tissue contacting surfaces of the jaws comprise an insulating material. A first electrode is housed within the first moveable jaw and a second electrode is housed within the second moveable jaw, where the electrodes are connectable to a power source for providing an electric current between the electrodes. When tissue is grasped between the tissue contacting surfaces, electrical current may be caused to flow between the electrodes and through the tissue grasped between the tissue contacting surfaces forming a first circuit.

The present invention further comprises a feedback light connectable to a first lead and a second lead in order to form a second circuit, where the second circuit is adjacent to the first circuit in order to facilitate capacitive coupling between the first and second circuits in order to light the feedback light. The present invention has application in conventional endoscopic and open surgical instrumentation as well application in robotic-assisted surgery.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 15 is a side plan view of an instrument according to the present invention incorporating a ratchet handle;

FIG. 16 is a side plan view of one half of an instrument in accordance with the present invention with detents and blade actuation improvements;

FIG. 19 is a side sectional view of the knife from the instrument illustrated in FIG. 16;

FIG. 20 is a top sectioned view of the jaw from the instrument illustrated in FIG. 16, showing that the jaw is curved;

FIG. 34 illustrates an electrical schematic of an electrosurgical instrument having a feedback light in accordance with the present invention;

FIG. 49 is a side view of the jaw illustrated in FIG. 47.

DETAILED DESCRIPTION OF THE INVENTION

Figure 2:
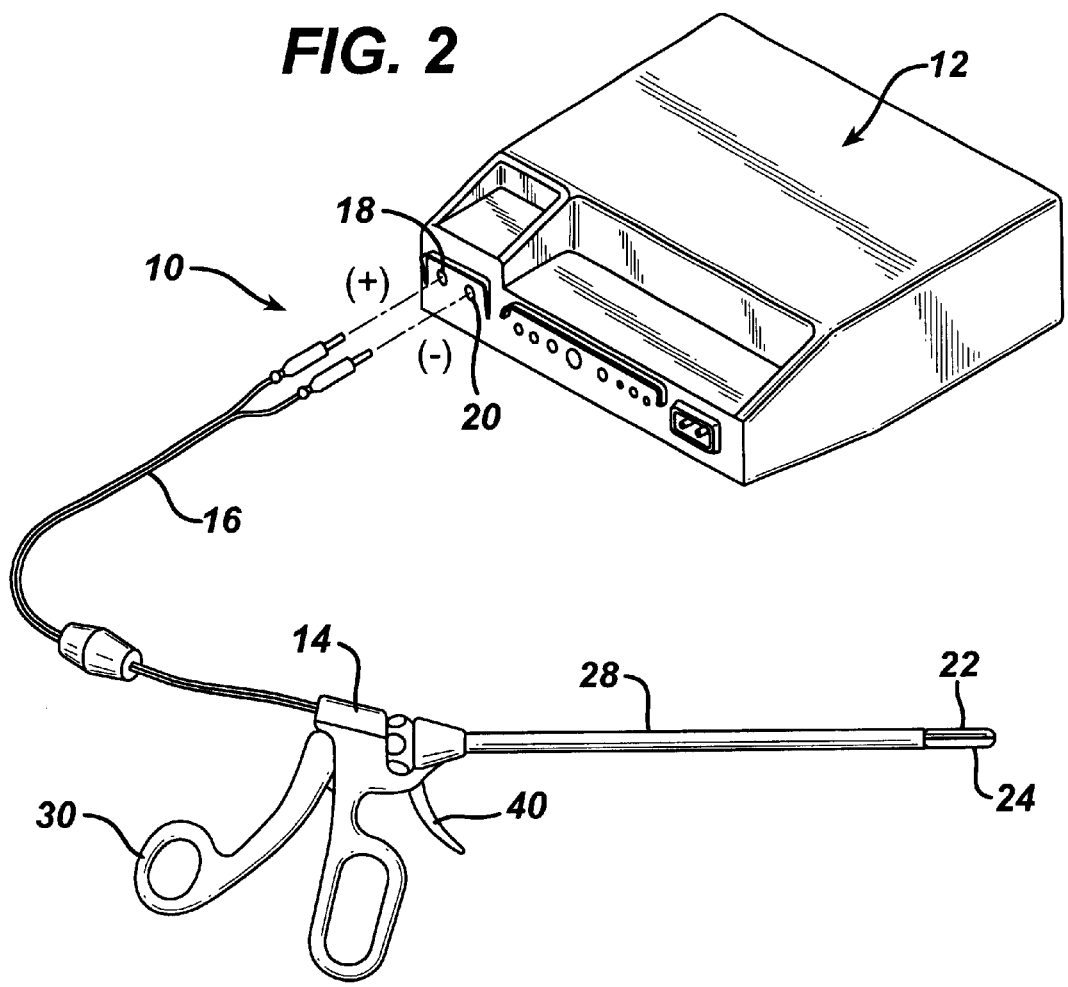
FIG. 2 is a perspective view of an endoscopic bipolar tissue grasper in accordance with the present invention shown with an associated electrosurgical current generating unit and connector table.

Turning to FIG. 2, there is seen a perspective view of an electrosurgical instrument system, generally designated 10, embodying the present invention. The illustrated system includes an RF energy generator 12, a hand-held, endoscopic electrosurgical graspers 14, and a cable 16 that connects the graspers 14 to the plug clip receptacles 18, 20 for positive and negative bipolar outputs of the generator 12. While the illustrated graspers 14 are endoscopic graspers for use in minimally invasive surgical procedures, the invention of the present application is equally applicable to graspers designed for use in open surgical procedures.

The illustrated RF generator 12 may be, for example, a unitary monopolar-bipolar RF generator, such as the PEGA-SYS (Trademark of Ethicon Endo-Surgery Inc., Cincinnati Ohio) generator, and thus also include plug clip receptacles for the mono-polar active and return terminals. However, for the purposes of the present invention, only the bipolar current generating feature is utilized.

The graspers 14 have two relatively moveable opposed jaws 22, 24, best seen in FIGS. 3 and 4a–4c. The general construction and mechanism for actuation of the graspers 14 is known in the art, and is typified by those graspers disclosed in U.S. Pat. Nos. 5,342,359 and 5,403,312. In general, a closure tube 26 is coaxially advanced through a sheath 28 by a trigger mechanism so as to engage a camming surface 32 on the jaws 22, 24 to close the jaws. Retraction of the closure tube moves the jaws to the open position (FIG. 4c) because the shape and material of the jaws 22, 24 springs open when the closure tube 26 retracts.

Figure 4A:
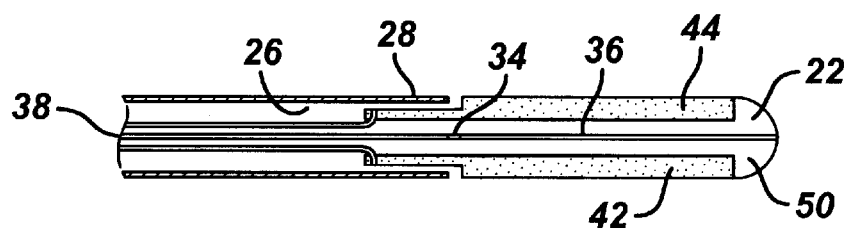
FIGS. 4a–c are top (FIG. 4a) and side (FIGS. 4b and c) views of the distal end of the graspers shown in FIG. 3, in partial cross-section to show the actuation mechanism for moving the grasper jaws between the closed (FIG. 4b) and open (FIG. 4c) positions.
Figure 4B:
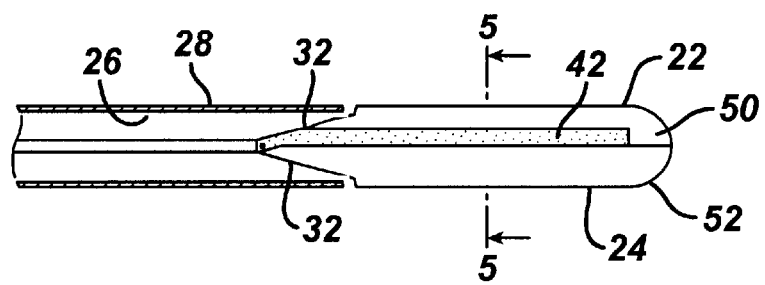
Figure 4C:
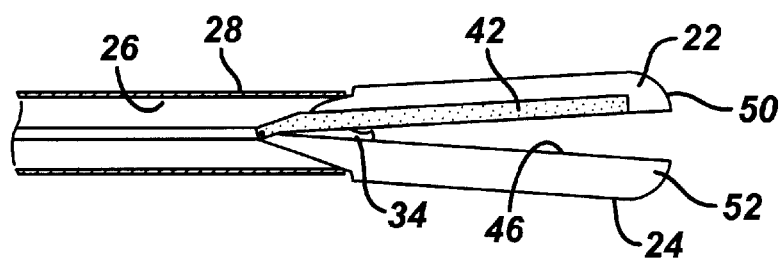
Figure 5:
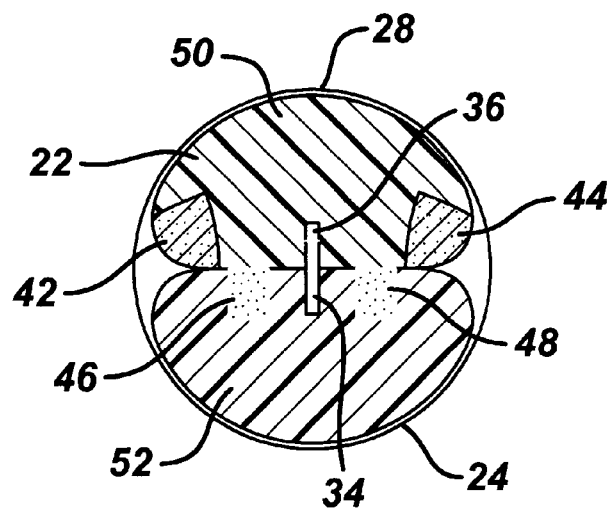
FIG. 5 is a cross-sectional view of the grasper jaws taken along line 5—5 of FIG. 4b.

The illustrated graspers also include a linear cutting element or knife 34 (best seen in FIGS. 4c and 5). Knife 34 is advanced into a slot 36 in the jaws 22, 24 to cut tissue held between jaws 22, 24 after the tissue has been coagulated. Again, the mechanism for advancing the knife is well known, and may include drive rod 38 that is advanced upon actuation of a trigger 40. While the illustrated graspers include a knife blade, the invention is equally applicable to simple graspers not including a cutting element.

In keeping with the present invention, each jaw includes a tissue contacting surface made of insulating material with two electrode surfaces carried adjacent the tissue contacting portions of each jaw. The tissue contacting surfaces of the jaws are in a generally face-to-face relationship, with the two electrodes associated with each jaw being spaced apart and in face-to-face relationship with the corresponding electrodes on the opposite jaw so that the electrodes in each offset face-to-face electrode pair is of a like polarity. This configuration for the electrodes, with the opposed electrodes in each offset face-to-face pair of electrodes being of the same polarity which is opposite to the polarity of the other offset face-to-face pair of electrodes, is similar to that shown in U.S. Pat. No. 2,031,682 to Wappler et al.

Figure 3:
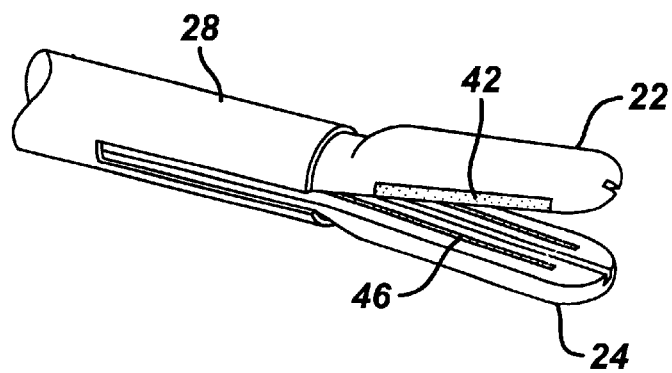
FIG. 3 is an enlarged perspective view of the distal end of the endoscopic bipolar tissue grasper of FIG. 2, showing the jaw members in greater detail.

Turning to FIGS. 3–5, the jaws 22, 24 include electrode pairs 42, 44 and 46, 48 respectively. The electrodes 42, 44 and 46, 48 are carried by the jaws 22, 24 adjacent the insulating members 50, 52, respectively. The insulating members 50, 52 form a tissue contacting surface on each jaw 22, 24 which is defined substantially by the surface on the insulating members 50, 52 that lies between their associated electrode pairs. However, the electrodes 42, 44 and 46, 48 also partially contact tissue grasped between the jaws.

Figure 6:
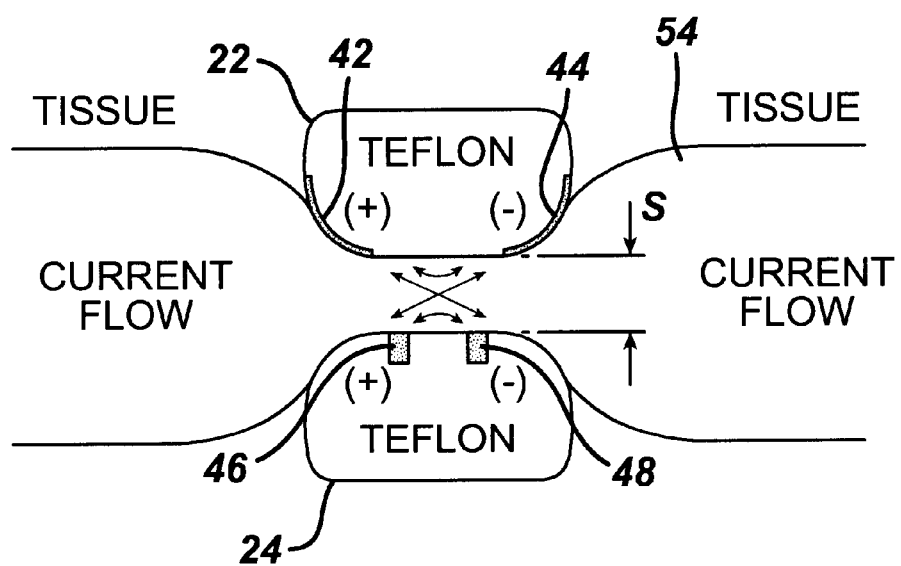
FIG. 6 is a cross-sectional view of the jaws of the inventive bipolar tissue graspers, with uncoagulated tissue disposed therebetween, showing the path of current flow between the two jaw members.
Figure 7:
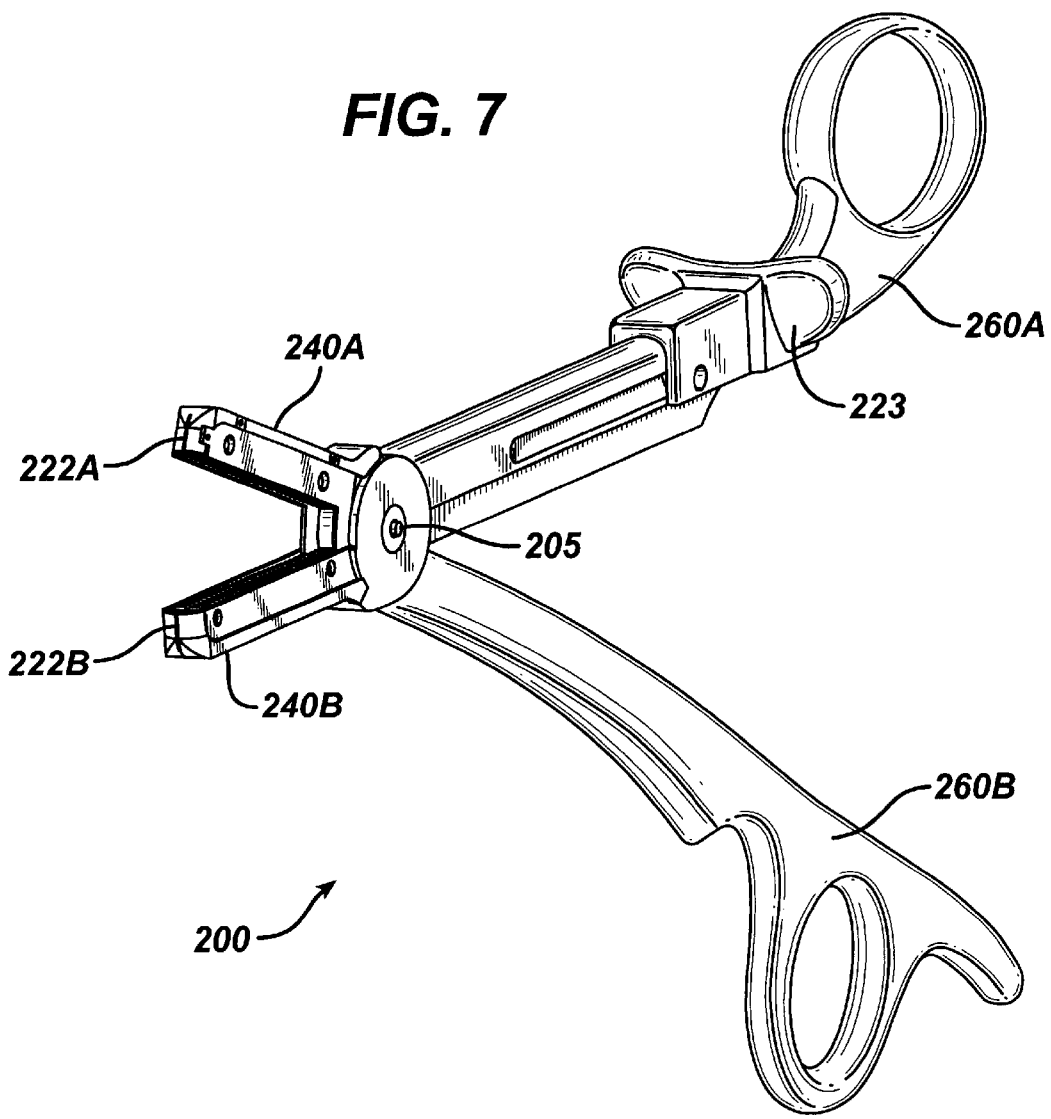
FIG. 7 is a perspective of an alternate embodiment of the present invention, a bipolar forceps in coagulation mode.
Figure 8:
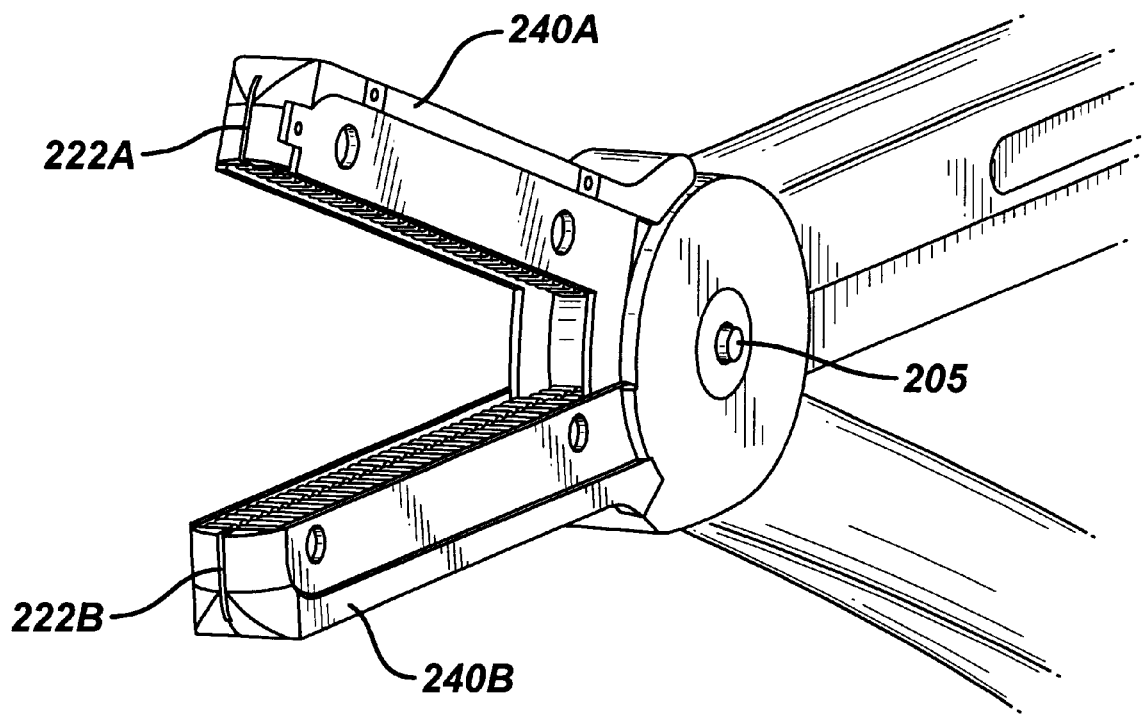
FIG. 8 is a perspective magnified view of the jaws illustrated in FIG. 7.
Figure 9:
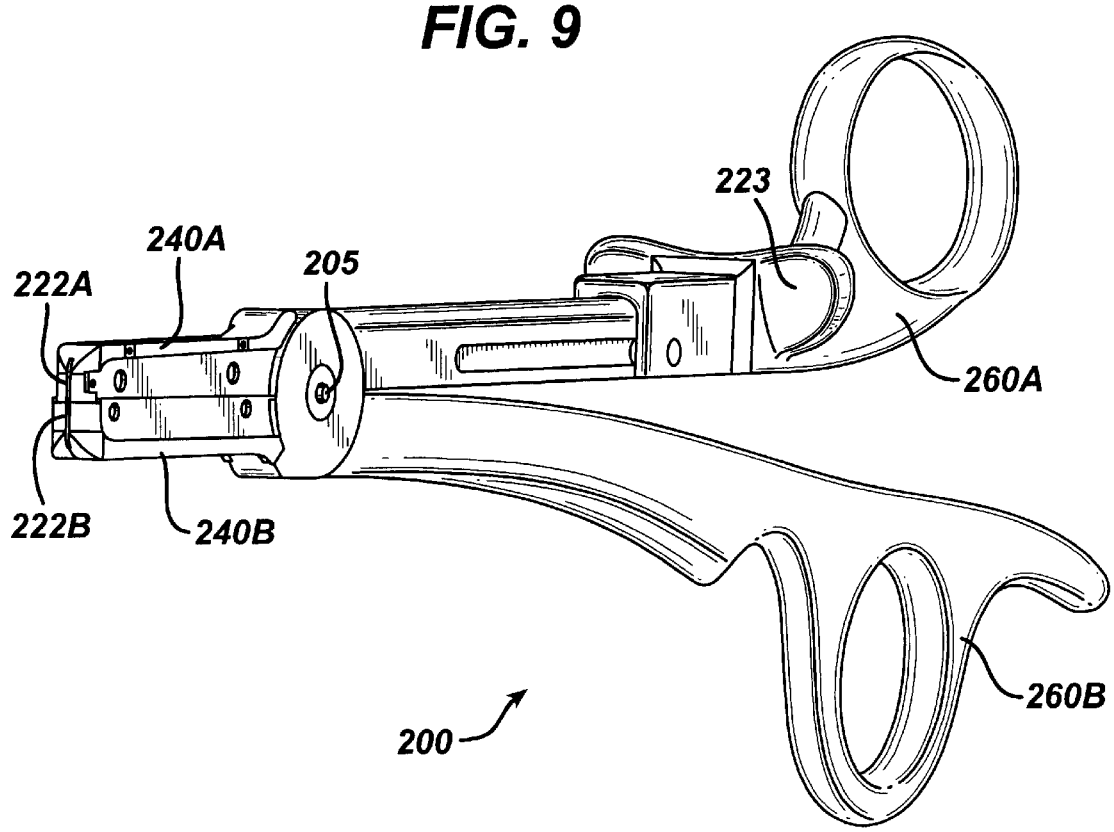
FIG. 9 illustrates the instrument of FIG. 7 in its closed position.

As best seen in FIG. 5, the tissue contacting surfaces of each jaw are in face-to-face relationship, and the electrodes are connected to the terminals of a bipolar RF generator so that the electrodes of each offset face-to-face pair are of the same polarity, and one offset face-to-face electrode pair is the opposite polarity of the other offset face-to-face electrode pair. Thus, as illustrated in FIGS. 5 and 6, offset face-to-face electrodes 42 and 46 are of a positive polarity, while offset face-to-face electrodes 44 and 48 are of a negative polarity. The term offset means that no portion of the surface areas of electrodes 42, 46, 44, and 48 are in an overlapping relationship.

Figure 1:
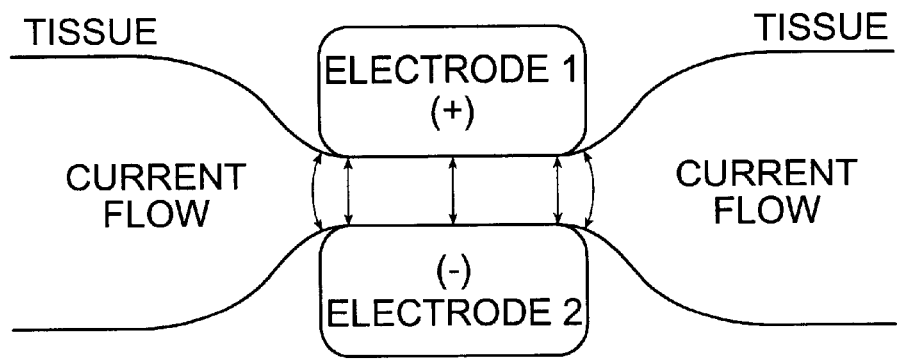
FIG. 1 is a cross sectional view of the jaws of the prior art bipolar graspers, with uncoagulated tissue disposed therebetween, showing the path of current flow between the two jaw members.

As shown in FIG. 6, this configuration of insulating members and electrodes provides for a current flow (as shown by the double-headed arrows) through the tissue 54 between the electrodes of opposite polarity. There is no current flow through the tissue that is not held between the grasper jaws, and the current flow is at its maximum density between the tissue contacting surfaces of the jaws. Accordingly, tissue is coagulated first along the center of the jaws and, as the impedance of the tissue increases due to its coagulation, the current flow between the electrodes is cut-off. Thus, the flow of current between the electrodes naturally stops when coagulation is complete. This is in marked contrast to the prior art bipolar graspers illustrated in FIG. 1, in which current flow continues through the tissue held outside of the jaws until such time as the operator deactivates the electrodes.

The insulating members 50, 52 comprising the tissue contacting surfaces are made of a non-stick, non-conductive material such as polytetreflouroethylene, polypropylene-polystyrene, polycarbonate, ABS (Acrylonitrile Butadiene Styrene), ULTEM (Trademark of General Electric Plastics), RADEL (Trademark of B.P. Amoco) or other suitable material. A substantially clear or transparent stick resistant insulating material permits the tissue held between the jaws to be viewed through the top or bottom surfaces of the jaw, thus allowing the operator to view the extent of tissue coagulation.

The electrodes 42, 44, 46, 48 are preferably made of a conductive material such as aluminum, stainless steel, platinum, silver, platinum, and gold. For better structural support, the electrodes themselves could be structural elements (as shown in FIGS. 3–5).

The graspers are constructed so that the clamped jaw spacing S is small enough relative to the electrode width to achieve a significantly higher current density in the tissue between the insulated surfaces than the current density through the tissue that contacts the electrode surfaces. This insures that current density at the electrodes is significantly less than the current density in the tissue held between the tissue contacting surfaces. Consequently, the tissue in contact with the electrodes will be coagulated less than the tissue held between the tissue contacting surfaces, and the tissue will be less likely to stick to the electrodes.

Figure 10:
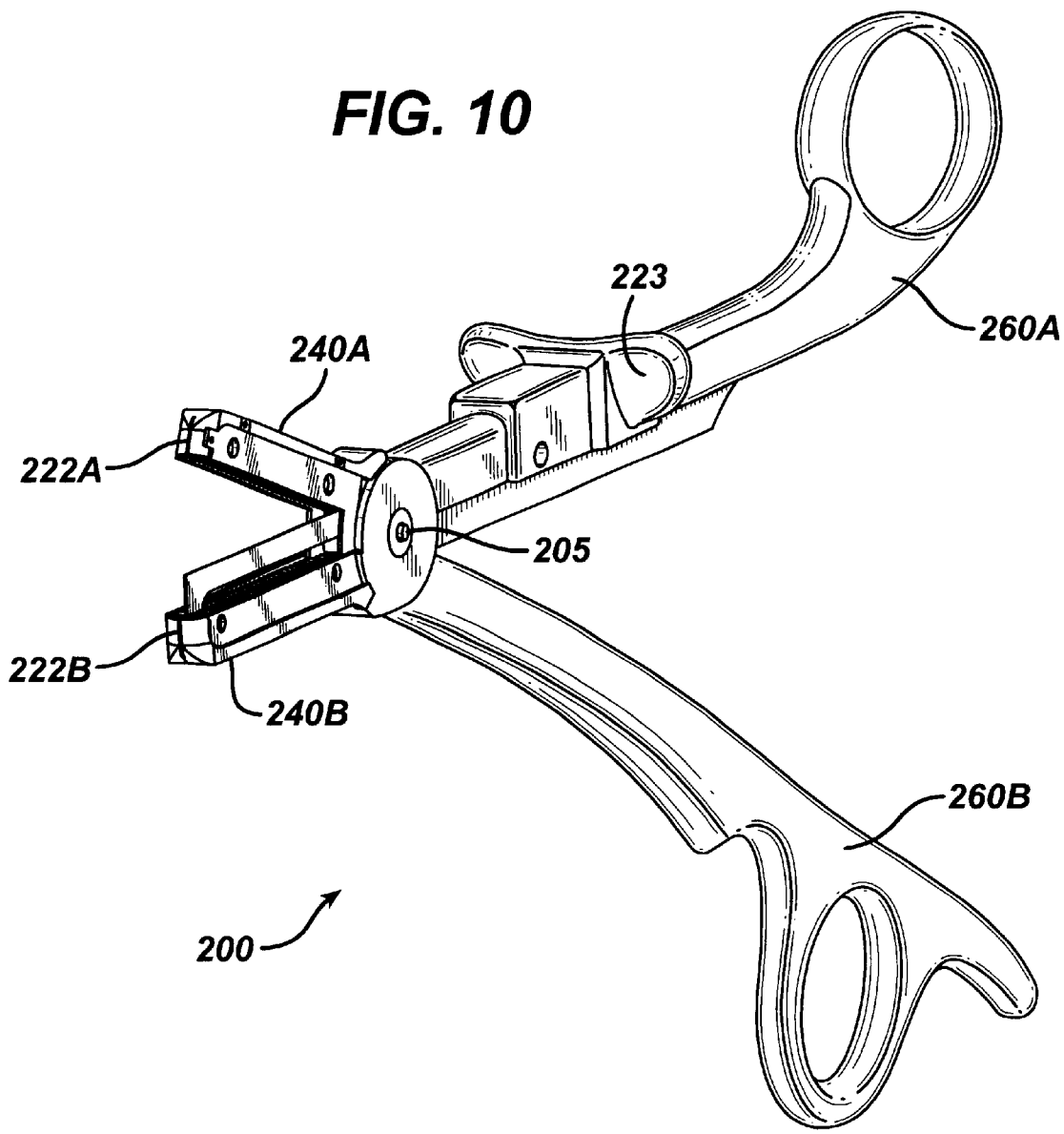
FIG. 10 illustrates the instrument of FIG. 7 in its scissors mode, jaws open.
Figure 11:
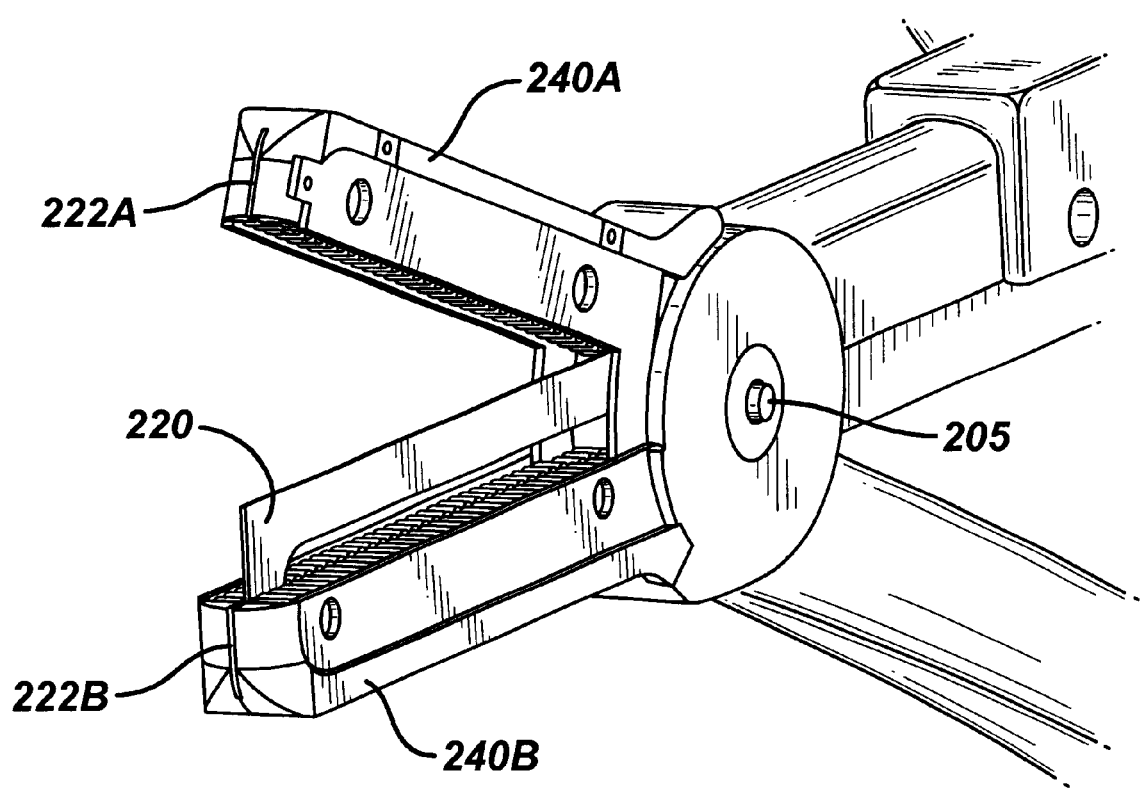
FIG. 11 is a perspective magnified view of the jaws illustrated in FIG. 10.

Other embodiments of the present invention are illustrated in FIGS. 7 through 23. Illustrated in FIGS. 7–11 is a forceps, a hemostat 200, that may be made, for example, of an electrically insulative plastic with filler for strength. The electrodes would be offset opposing with like polarity that minimizes lateral thermal tissue damage, such as, for example, those illustrated in FIG. 12. This electrode configuration eliminates shorting of the electrodes when fully closed and minimizes tissue sticking. The hemostat 200 may also incorporate a blade, designated sliding knife 220 (see, for example, FIG. 11), for cutting tissue after coagulation. Additionally, when using the instrument in the scissors mode as illustrated in FIGS. 10 and 11, the sliding knife 220 would be extended out (unenergized) and the tissue would be mechanically cut between the upper surface of the blade and the opposing jaw of the instrument.

The offset opposed electrode configuration offers a current limiting feature. As tissue becomes desiccated, the impedance to the current flow increases which will shut the system down when the coagulation is complete. Each jaw 240 of the instrument incorporates positive and negative electrodes. The opposing jaws 240A and 240B consist of a pair of offset opposing electrodes with like polarity for providing the proper tissue effects and preventing tissue sticking due to the electrodes not physically being able to touch each other when fully closed. The tissue is coagulated from the current flowing between the opposite polarity electrodes on each jaw 240. In the scissors cutting mode the upper edge of the sliding knife 220 many be sharpened to improve the cutting capability. The sliding knife 220 may be locked in the extended position until one changes it over to bipolar cutting/coagulating mode.

An advantage of this invention is a coagulation and cutting forceps, which has current limiting electrodes that deliver the proper amount of current to coagulate tissue (minimal lateral thermal spread) along with a mechanical scissors mode without instrument interchange.

The electrodes may be insert molded into the jaws 240. Hemostat 200 has two opposing jaws 240A and 240B, joined in a cross-over fashion by a pivot feature such as pin 205. Each jaw 240 has an opposing tissue compression zone with two electrodes along the length of each compression zone as more fully described in FIGS. 44–49.

Figure 12:
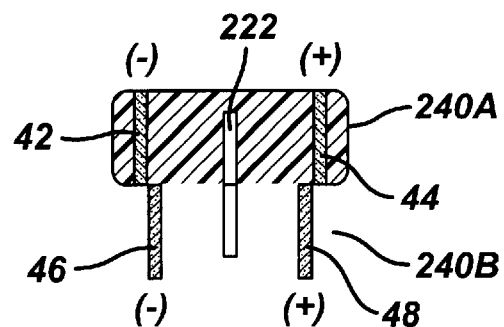
FIG. 12 is a cross sectional view of jaws from a bipolar instrument having offset opposed electrodes in accordance with the present invention.
Figure 21:
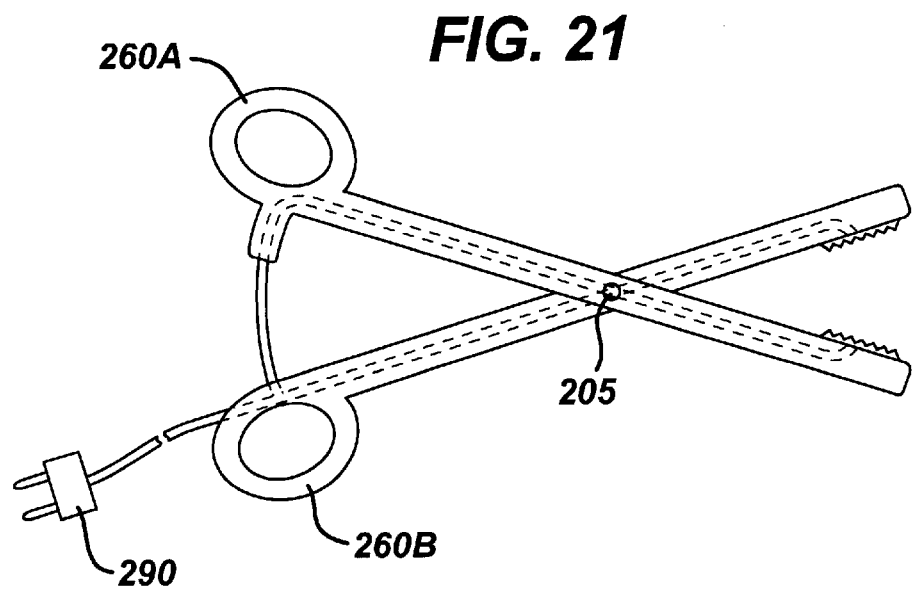
FIG. 21 illustrates an instrument in accordance with the present invention showing the connector and wire layout for a bi-polar instrument.

The user interface portion of hemostat 200 would contain opposable handles 260A and 260B for actuation. The user interface portion may also include a means of connection to an electrosurgical generator such as, for example, connector 290 (FIG. 21). The desired electrode configuration should be an electrode of each polarity in each compression member. The opposing electrodes in opposing compression members would be of like polarity as illustrated in FIG. 12. This offset electrode configuration is desirable because it eliminates shorting on thin tissue as well as limits thermal spread. The thermal spread is limited by the current flow. The current flow is maintained within the aperture of the device. In addition, this electrode configuration offers a limiting feature. As the tissue becomes desiccated, the impedance to current flow increases. Because the current flow is maintained within the jaws, when the impedance in the tissue gets high enough the system will shut itself down.

Referring again to FIG. 11, a forceps in accordance with the present invention may additionally have a sliding knife 220 added to sever tissue following cauterization. The device may include a ratchet mechanism 288 (FIG. 13) near the ring handles 260A and 260B (such as, for example, those shown in FIG. 7) in order to provide the surgeon with a method of setting clamp pressure. Both forcep members may include a slot 222, (designated 222A or 222B on individual forcep members) positioned parallel to the electrodes and centered between the electrodes. One of the forcep members may have an extended slot (toward ring handle) in order to accommodate the sliding knife 220 and it's movement. The sliding knife 220 may include a cutout or slot 221 in order to allow movement with respect to the forcep pivot pin 205 along the forcep jaw 240. In addition, the sliding knife 220 may include a feature to provide actuation force to the sliding knife 220 (i.e. a slide button 223). As shown in FIGS. 19 and 20, the knife 220 may include grooves 266 to accommodate a curved jaw 240.

Figure 13:
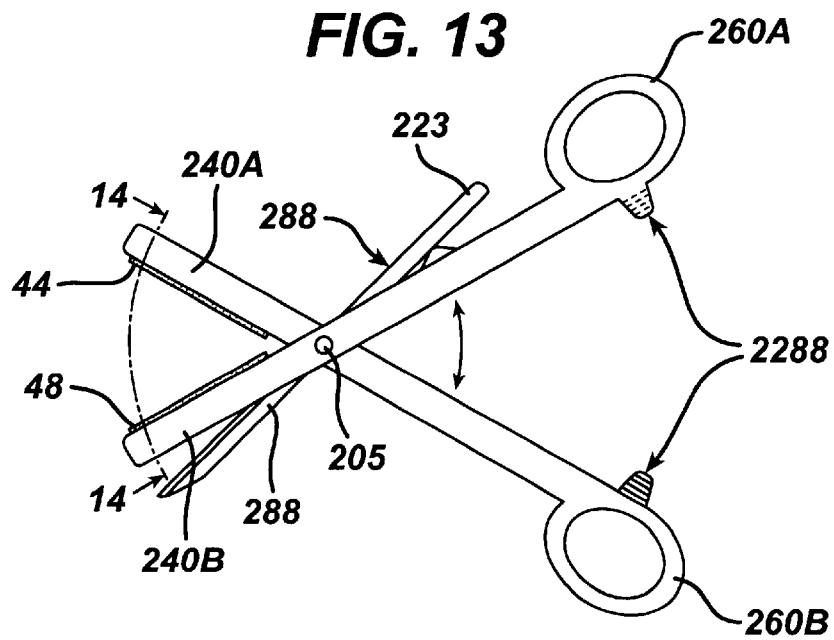
FIG. 13 is a side plan view of an alternate embodiment of a combination grasping/cutting instrument in accordance with the present invention.
Figure 14:
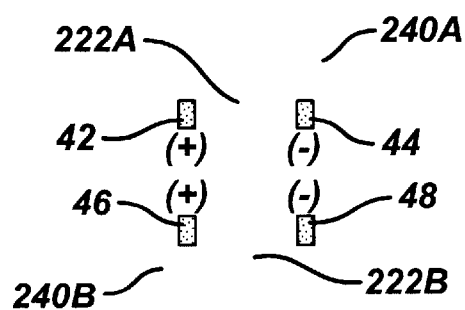
FIG. 14 is a cross-sectional view of the jaws of the instrument illustrated in FIG. 13.
Figures 17, 18:
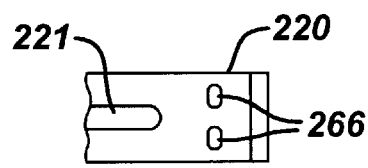
FIG. 17 is a top sectional view taken from the part of FIG. 16.
FIG. 18 is an alternate top sectional view taken from the part of FIG. 16.

The hemostat 200 may include a scissors cutting member 288 that is spring loaded open and works off of the same pivot as the forceps, as illustrated in FIG. 13. Both forcep members may include slots through the tissue contact areas parallel to and centered between the electrodes. The scissors cutting member may be sharp at the tissue interface edge and reside within one of the forcep members. The forcep members may include a ratchet mechanism 2288 near the ring handles in order to provide the surgeon with a method for maintaining clamp pressure.

Figure 22:
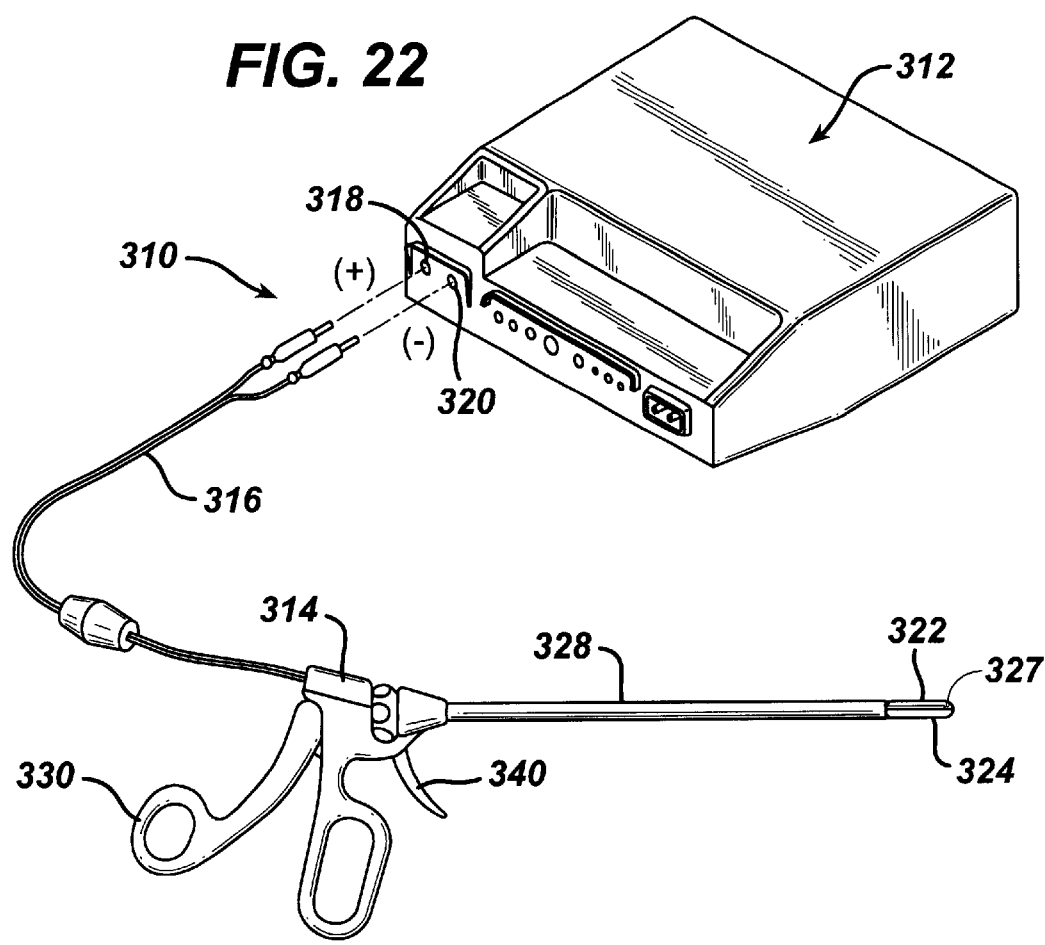
FIG. 22 is a perspective view of an electrosurgical instrument having a feedback light in accordance with the present invention shown with an associated electrosurgical current generating unit and connector table.
Figure 23:
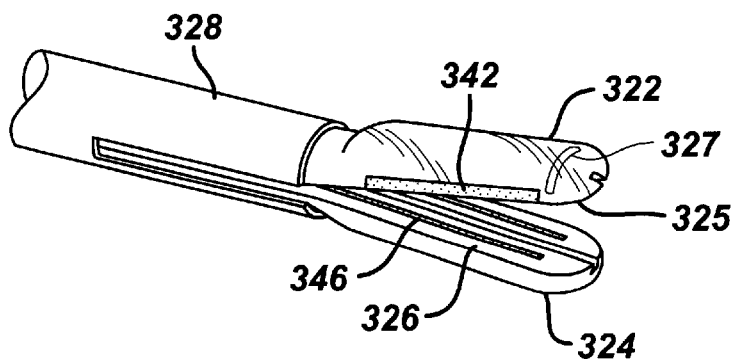
FIG. 23 is an enlarged perspective view of the distal end of the electrosurgical instrument having a feedback light of FIG. 22, showing the jaw members in greater detail.

FIGS. 22–30 illustrate an electrosurgical instrument system, generally designated 310, an alternate embodiment of the present invention. The features of the illustrated system correspond to like features of the embodiment shown in FIGS. 2–6, but referenced with "300" series element numbers for similar features. New numbers are added for newly presented features. FIG. 22 further illustrates a feedback light 327 that, in one embodiment of the present invention, is housed within one or both of first and second moveable jaws 322, 324. Feedback light 327 will be further described below.

The present invention illustrates a feedback light 327 used in cooperation with first moveable jaw 322, where feedback light 327 indicates to the operator of the electrosurgical instrument system 310 when a significant electric current is no longer passing through tissue 354 held between first moveable jaw 322 and second moveable jaw 324. In a further embodiment of the present invention feedback light 327 is housed within first moveable jaw 322, where first moveable jaw 322 is constructed from a substantially transparent material so as to allow the operator to view the light housed within first moveable jaw 322. Feedback light 327 may be found on any portion of first and/or second moveable jaws 322, 324, a plurality of feedback lights 327 may be found on electrosurgical instrument system 310, and/or feedback light 327 may be located externally to first and/or second moveable jaws 322, 324, where feedback light 327 is permanently or removably affixed to first and second moveable jaws 322, 324. Feedback light 327 may be constructed in a variety of forms such as, for example, oval, square, looped, square, or rectangular, and may be any color desirable.

Figure 24:
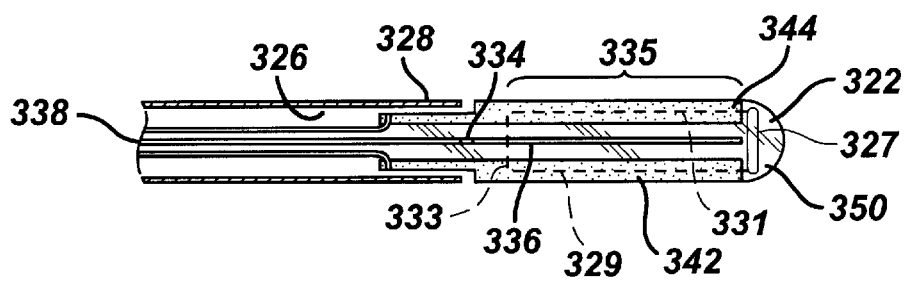
FIGS. 24–26 are top (FIG. 24) and side (FIGS. 25 and 26) views of the distal end of the jaws shown in FIG. 23, in partial cross-section to show the actuation mechanism for moving the jaws between the closed (FIG. 25) and open (FIG. 26) positions and the accompanying feedback light.
Figure 25:
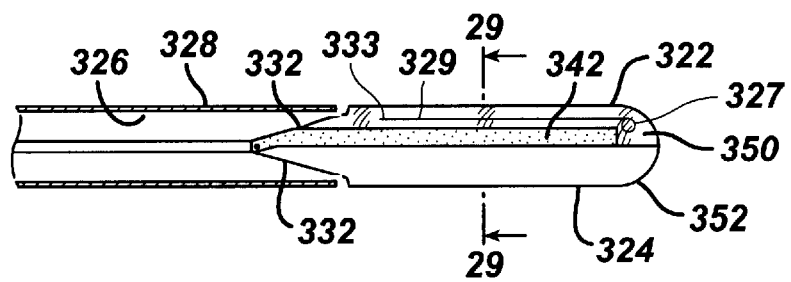
Figure 26:
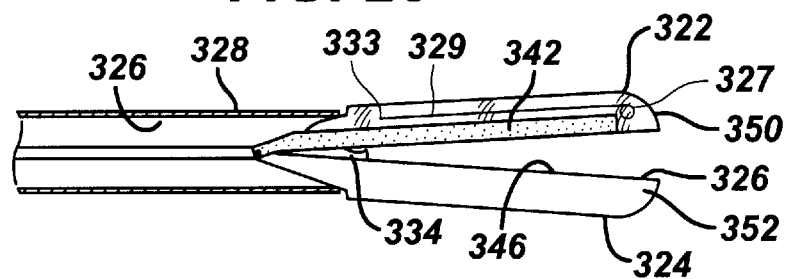
Figure 27:
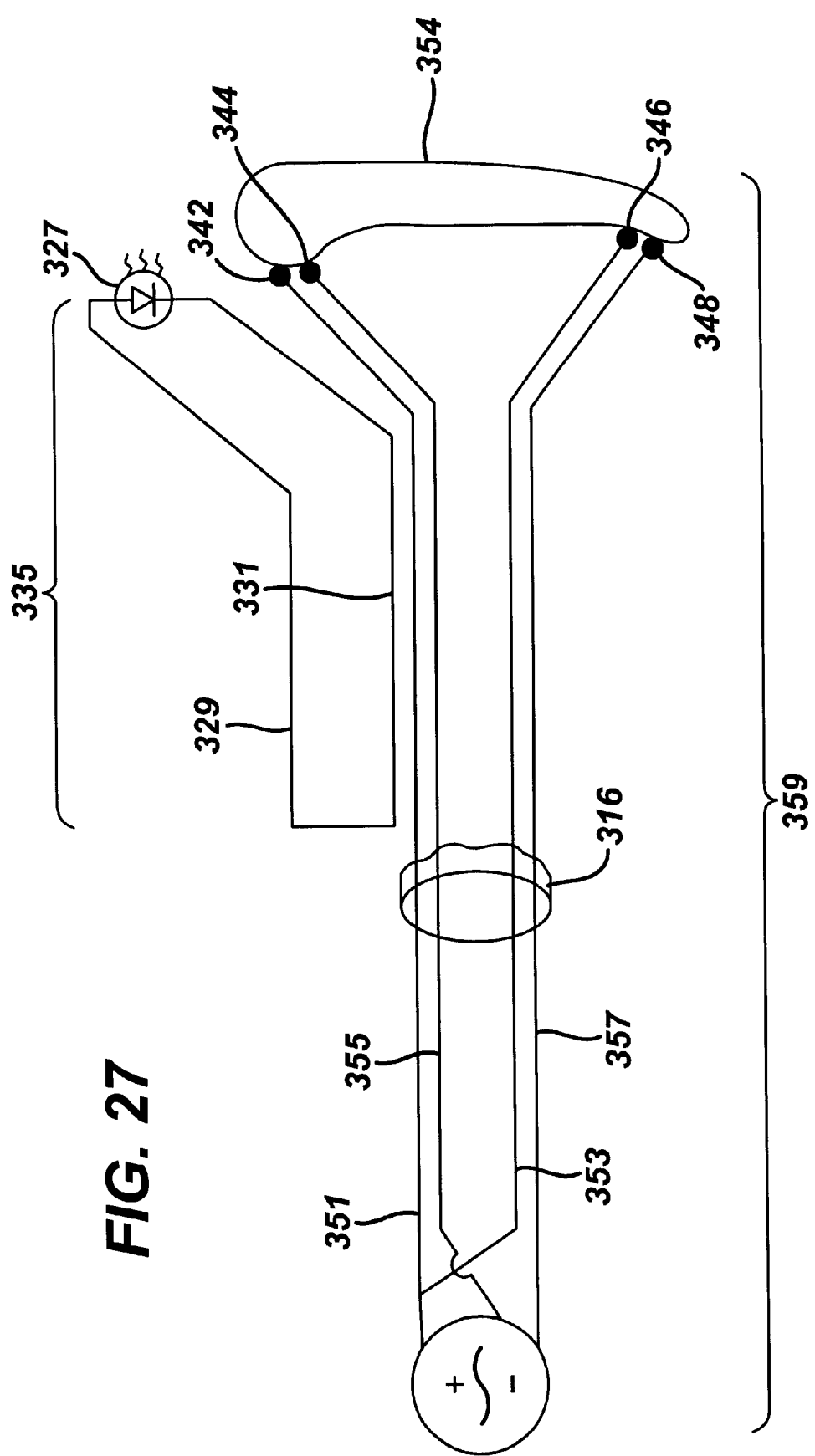
FIG. 27 illustrates an electrical schematic of an electrosurgical instrument having a feedback light in accordance with the present invention.

FIGS. 24–26 illustrate a means of operating the electrosurgical instrument system 310 in accordance with the present invention. In general, a closure tube 326 is coaxially advanced through a sheath 328 by a trigger mechanism 330 so as to engage a camming surface 332 on the first and second moveable jaws 322, 324 to close first and second moveable jaws 322, 324. Retraction of the closure tube 326 moves the first and second movable jaws 322, 324 to the open position because the shape and material of the first and second moveable jaws 322, 324 springs open when the closure tube 326 retracts. FIGS. 24–26 illustrate one embodiment of the present invention comprising a first feedback light 327, a first lead 329 and a second lead 331 where first feedback light 327, first lead 329 and second lead 331 form an untwisted circuit 335. First and second leads 329, 331 run parallel to cable 316 (FIG. 27). First feedback light 327 may be any light emitting device such as, for example, an LED (light emitting diode). First and second leads 329, 331 may be constructed from any conductive material suitable for use in surgical applications such as, but not limited to, silver or stainless steel.

Referring to FIGS. 27–30, the present invention may also include variations in circuit design such as, for example, leads 329, 331 that extend along the entire length of closure tube 326, a plurality of leads 329, 331, and/or a plurality of feedback lights 327. In one embodiment of the present invention, untwisted circuit 335 is parallel to, but not connectively coupled with cable 316. First feedback light 327 is adapted for illumination when current is passed through circuit 335. Bipolar current delivered between electrodes 342, 344, 346, 348 conducts through tissue 354 until tissue 354 is desiccated. Once desiccated, tissue 354 impedance increases reducing the voltage passing through untwisted circuit 335. By passing the leads 351, 353, 355, 357 of cable 316 and first and second leads 329, 331 down a length of closure tube 326 without twisting first and second leads 329, 331, a capacitive coupling will be created between the two circuits. As power is applied to the leads 351, 353, 355, 357 of cable 316, they will create a current in untwisted circuit 335 that will cause feedback light 327 to light. The current in untwisted circuit 335 will be proportional to the current in the leads of cable 316, giving the operator a qualitative indicator of power passing through the instrument.

Figure 29:
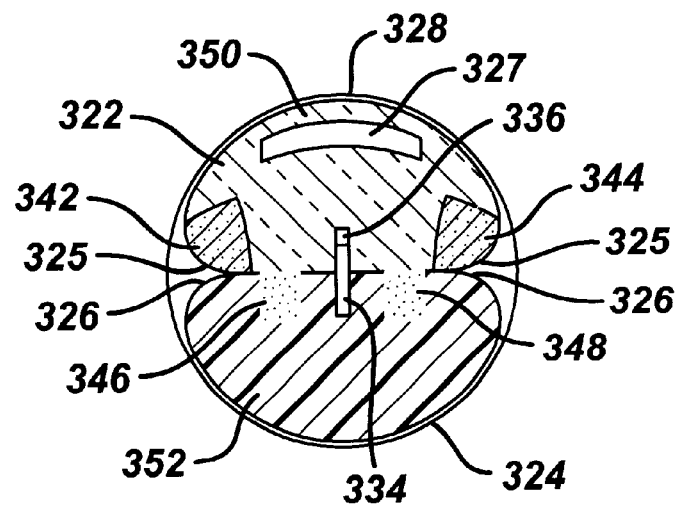
FIG. 29 is a cross sectional view of the jaws (FIG. 23) of an electrosurgical instrument having a feedback light in accordance with the present invention.
Figure 30:
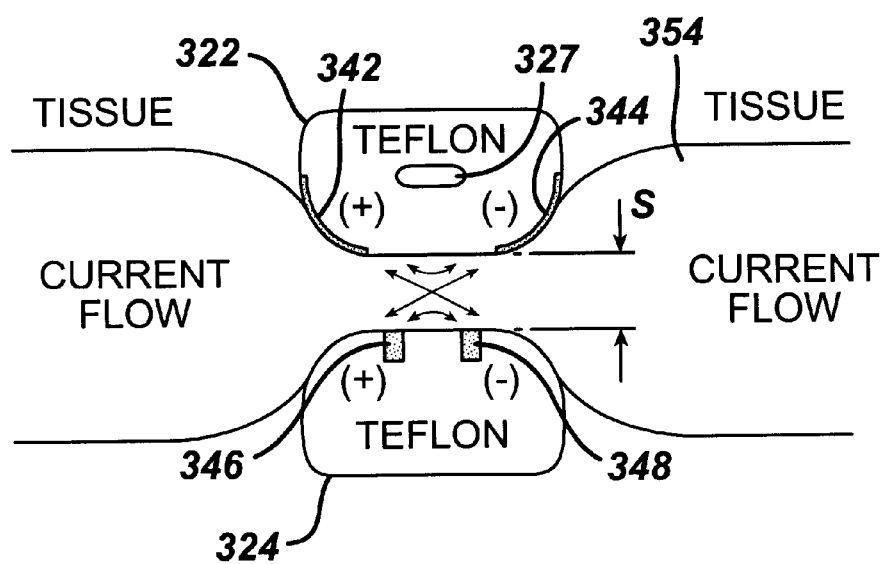
FIG. 30 is a cross-sectional view of the jaws of the electrosurgical instrument having a feedback light, with uncoagulated tissue disposed therebetween, showing the path of current flow between the two jaw members.

The illustrated first and second moveable jaws 322, 324 may also include a linear cutting element or knife 334 (best seen in FIGS. 26 and 29). Knife 334 is advanced into a slot 336 in the first and second moveable jaws 322, 324 to cut tissue 354 held between the first and second moveable jaws 322, 324 after the tissue 354 has been coagulated. Again, the mechanism for advancing the knife is well known, and may include drive rod 338 that is advanced upon actuation of a trigger 340. While the illustrated first and second moveable jaws 322, 324 include a knife blade, the invention is equally applicable to simple jaws not including a cutting element.

The distal placement of feedback light 327, in close proximity to the area of surgical application, provides the operator with a clear indicator of when tissue 354 has been sufficiently desiccated to insure proper hemostasis while reducing lateral damage due to over exposure of electric current. The present invention further may also include the use of feedback light 327 in cooperation with all other bipolar electrosurgical devices such as, for example, instruments having a single pair of electrodes.

FIG. 27 illustrates a electrical schematic of one embodiment of the present invention illustrating RF generator 312, where RF generator 312 is connected to electrodes 342, 344, 346, 348 via leads 351, 355, 353, 357, respectively. In one embodiment of the present invention, electrodes 342, 344, 346, 348 are adapted, as illustrated, for electrodes 342, 346 to be positive electrodes in an off-set but substantially face-to-face arrangement. Electrodes 344, 348 are adapted, as illustrated, to be negative electrodes in an off-set but substantially face-to-face arrangement. Further embodiments of the present invention may include the use of a single off-set pair of electrodes, a single pair of aligned electrodes, a plurality of electrodes and their accompanying plurality of leads, a plurality of aligned electrodes, a pair or a plurality of electrodes of like polarity arranged opposedly as opposed to a face-to-face arrangement, or any other bipolar configuration suitable for use in a surgical application. FIG. 27 further illustrates untwisted circuit 335 comprising first and second leads 329, 331, and feedback light 327. The present invention may also include a means of lighting feedback light 327 when a complete circuit is made between electrodes 342, 344, 346, 348 leads 351, 353, 355, 357, tissue 354 and, generator 312, by capacitively coupling second lead 331 and/or first lead 329 to at least one lead 351, 353, 355, 357 resulting in the introduction of a current into untwisted circuit 335. When tissue 354 desiccates, it will increase the impedance of the transmission circuit resulting in a loss of current transmitted by capacitive coupling, causing the feedback light 327 to dim or turn off. Dimming, or inactivity of feedback light 327 signals the operator to cease applying electrosurgical current to tissue 354 in order to prevent burns or lateral tissue damage. The present invention may also include other features necessary to facilitate the capacitive coupling of circuit 335 such as, capacitors, resistors, relays, transformers, switches, or other suitable electrical features.

Figure 28:
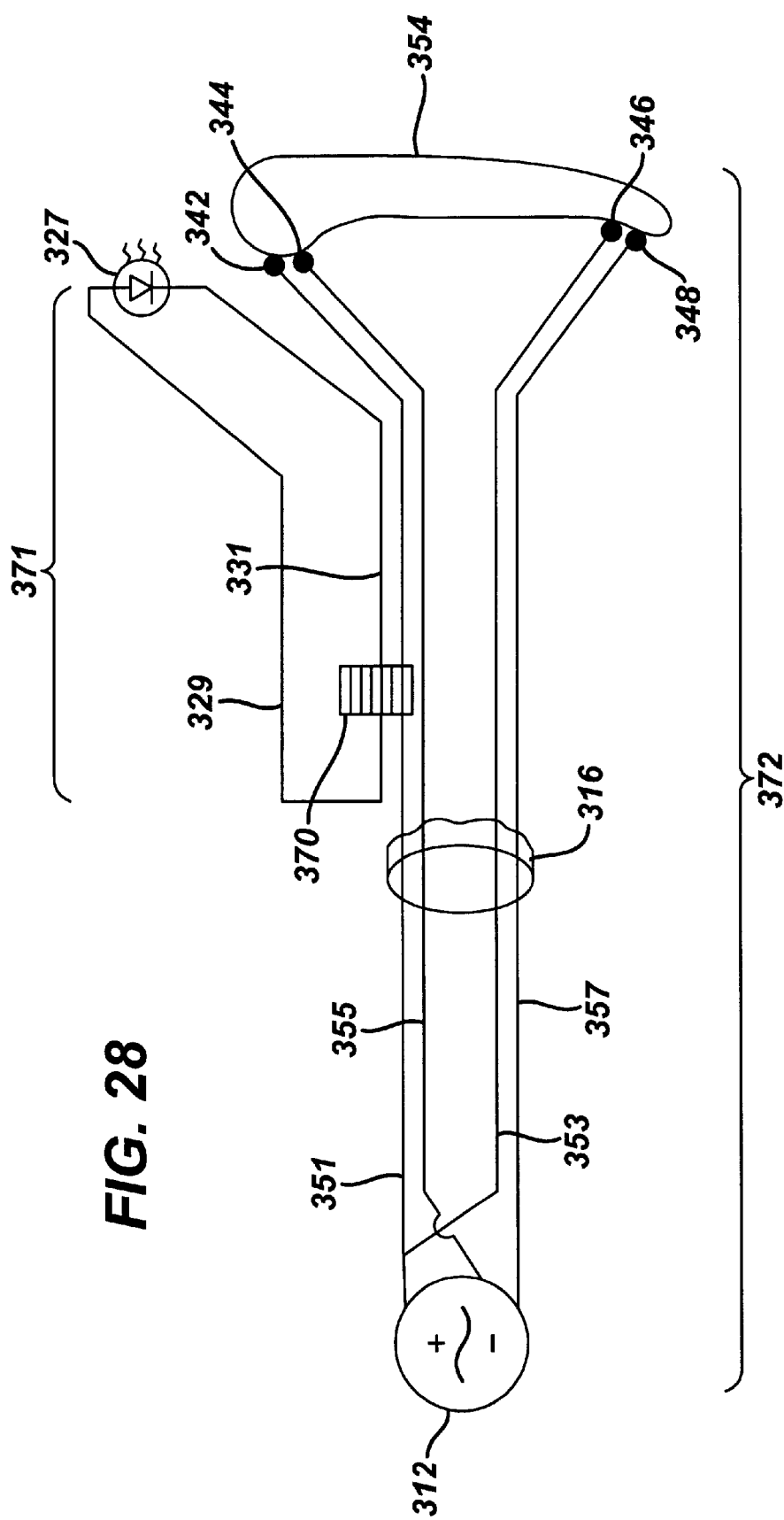
FIG. 28 illustrates an electrical schematic of an alternated electrosurgical instrument having a feedback light in accordance with the present invention.

FIG. 28 illustrates an electrical schematic of a further embodiment of the present invention comprising RF generator 312, where RF generator 312 is connected to electrodes 342, 344, 346, 348 via leads 351, 355, 353, 357, respectively. In one embodiment of the present invention, electrodes 342, 344, 346, 348 are adapted, as illustrated, for electrodes 342, 346 to be positive electrodes in an off-set, but substantially face-to-face arrangement. Electrodes 344, 348 may be adapted to be negative electrodes in an off-set but substantially face-to-face arrangement. Further embodiments of the present invention may include the use of a single off-set pair of electrodes, a single pair of aligned electrodes, a plurality of electrodes and their accompanying plurality of leads, a plurality of aligned electrodes, and/or electrodes of like polarity arranged oppsedly as opposed to a face-to-face arrangement, or other bipolar configurations suitable for use in a surgical application. FIG. 28 further illustrates twisted circuit 371 comprising first and second leads 329, 331, toroid 370, and feedback light 327. Second lead 331 may be wound around toroid 370 in order to facilitate inductive coupling between at least one lead 351, 353, 355, 357 and toroid 370. Electric current passing through at least one lead 351, 353, 355, 357 will create a magnetic field which may then be converted into electric current in twisted circuit 371 by toroid 370. Twisted Circuit 371 and/or twisted transmission circuit 372 may be twisted in order to reduce capacitive coupling between twisted circuit 371 and twisted transmission circuit 372. The present invention may also include a means of lighting feedback light 327 when a complete circuit is made between electrodes 342, 344, 346, 348 leads 351, 353, 355, 357, tissue 354 and, generator 312 by inductively coupling second lead 331 and/or first lead 329, in cooperation with toroid 370, to at least one lead 351, 353, 355, 357, resulting in the introduction of a current into twisted circuit 371. As tissue 354 desiccates, it will increase the impedance of the transmission circuit resulting in a loss of current transmitted by inductive coupling, causing the feedback light 327 to dim or turn off. Dimming, or inactivity of feedback light 327 signals the operator to cease applying electrosurgical current to a tissue in order to prevent burns or lateral tissue damage. The present invention may also include other features necessary to facilitate the inductive coupling of circuit 371 such as, capacitors, resistors, relays, transformers, switches, or other suitable electrical features.

Figure 31:
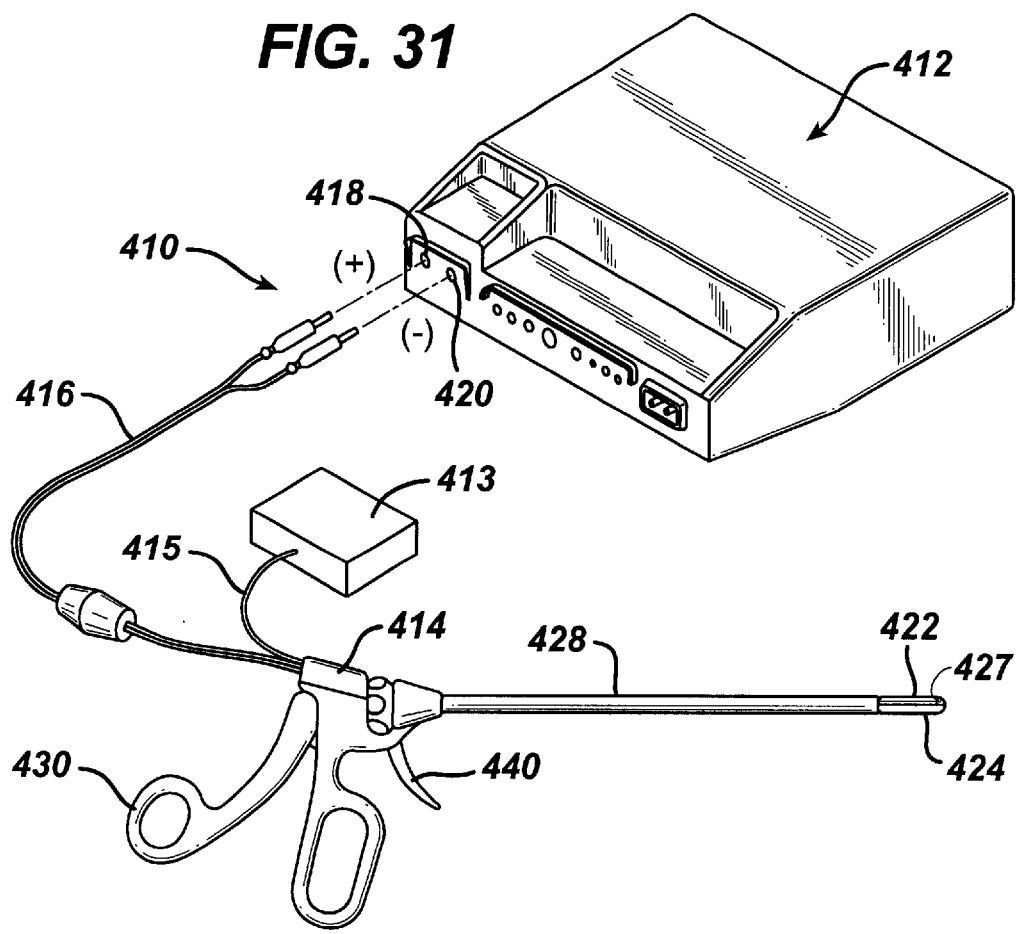
FIG. 31 is a perspective view of an electrosurgical instrument having a feedback light in accordance with the present invention shown with an associated electrosurgical current generating unit and connector cable and associated biased power source and a connector cable.
Figure 32:
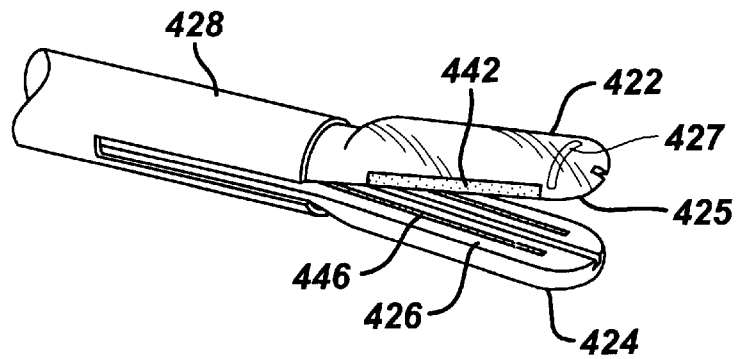
FIG. 32 is an enlarged perspective view of the distal end of the electrosurgical instrument having a feedback light of FIG. 22, showing the jaw members in greater detail.
Figure 33A:
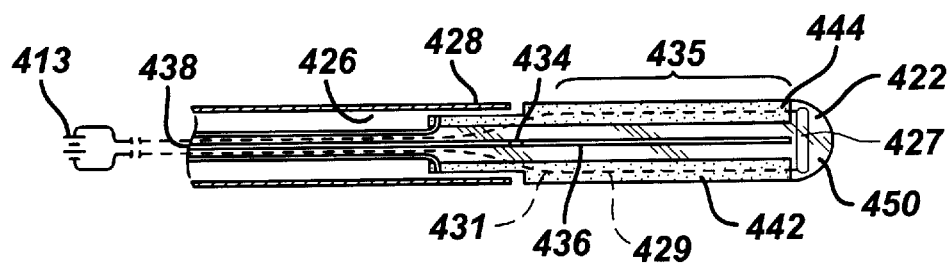
FIGS. 33a–c are top (FIG. 33a) and side (FIGS. 33b and c) views of the distal end of the jaws shown in FIG. 32, in partial cross-section to show the actuation mechanism for moving the jaws between the closed (FIG. 33b) and open (FIG. 33c) positions and the accompanying feedback light.
Figure 33B:
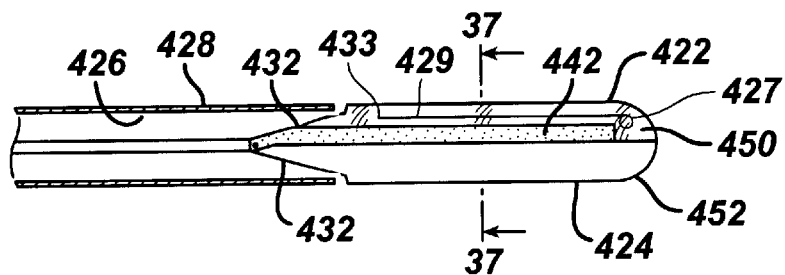
Figure 33C:
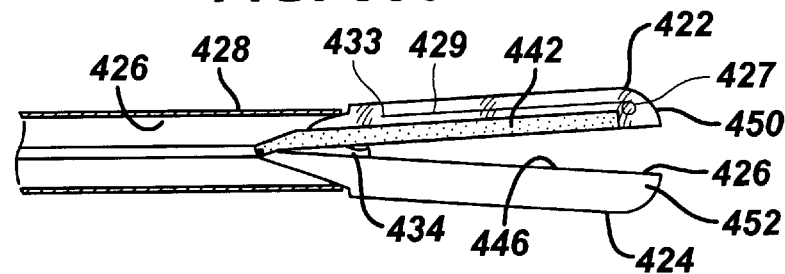

FIGS. 31–38 illustrate an electrosurgical instrument system, generally designated 410, an alternate embodiment of the present invention. The features of the illustrated system correspond to like features of the embodiment shown in FIGS. 2–6, but referenced with "400" series element numbers for similar features. As before, new numbers are added for newly presented features. FIG. 31 illustrates a perspective view of one embodiment of the present invention comprising an electrosurgical instrument system, generally designated 410, including an RF energy generator 412, housing 414, and a cable 416 that connects the housing 414 to the positive bipolar output plug clip receptacle 418, and negative bipolar output plug clip receptacle 420 of the generator 412, where the cable 416 is adapted to transmit electric current to electrodes 442, 444 housed within first moveable jaw 422 and to electrodes 446, 448 housed within second moveable jaw 424, and a battery 413 having a cable 415. The battery 413 may be any power source suitable for use with a particular surgical application such as, for example, a 5 volt battery. Battery 413 may be incorporated into housing 414 or may be located externally to housing 414. FIG. 31 further illustrates a feedback light 427 that, in one embodiment of the present invention, is housed within one or both of first and second moveable jaws 422, 424. Feedback light 427, battery 413, and cable 415 will be further described below.

FIGS. 33a–c and 34 illustrate one embodiment of the present invention comprising a first feedback light 427, a first lead 429, a second lead 431, and a battery 413, where first feedback light 427, first lead 429, second lead 431, and battery 413 form an untwisted circuit 435. First and second leads 429, 431 may run parallel to cable 416. First feedback light 427 is connected to battery 413 via cable 415 that houses first and second leads 429, 431. Battery 413 may be located externally in relation to housing 414 or may be housed internally. First feedback light 427 may be any light emitting device such as, for example, an LED (light emitting diode). First and second leads 429, 431 may be constructed from any conductive material suitable for use in surgical applications such as, but not limited to, silver or stainless steel. The present invention may also include variations in circuit design such as, for example, a plurality of first and second leads 429, 431 and/or a plurality of feedback lights 427. In the illustrated embodiment, first and second leads 429, 431 are parallel to, but not connectively coupled with leads 451, 453, 455, 457 housed within cable 416. Battery 413 is a biased power source delivering direct current at a voltage lower than necessary to light feedback light 427. The use of battery 413 in cooperation with feedback light 427 provides a tuning capability allowing the operator to control how much energy is required for the feedback light 427 to light. For example, by setting the voltage delivery of battery 413 at just below the threshold needed to light feedback light 427, the operator will easily cross the threshold even as impedance continues to increase. If a lower voltage delivery from battery 413 is chosen, in cooperation with the same first feedback light 427, the voltage of untwisted circuit 435 may drop below the threshold required to keep feedback light 427 lit with only a minimal amount of impedance. Using a variety of voltage deliveries from a battery 413 in cooperation with the choice of a variety of different feedback lights having different lighting thresholds allows for the operator to choose the optimal set-up for a particular surgical application. First feedback light 427 is adapted for illumination when current is passed through untwisted circuit 435. Bipolar current delivered between electrodes 442, 444, 446, 448 conducts through tissue 454 until tissue 454 is desiccated. Once desiccated, tissue 454 no longer conducts current and will therefore increase the impedance in the untwisted transmission circuit 459 between electrodes 442, 444, 446, 448. By passing the leads 451, 454, 455, 457 of cable 416, and first and second leads 429, 441 down a length of closure tube 426 without twisting first and second leads 429, 441, a capacitive coupling will be created between the two circuits. As power is applied to the leads 451, 453, 455, 457 of cable 416, they will increase the voltage in the untwisted circuit 435 causing feedback light 427 to light. The current in untwisted circuit 435 will be proportional to the current in the leads of cable 416, giving the operator a qualitative indicator of power passing through the instrument.

Figure 37:
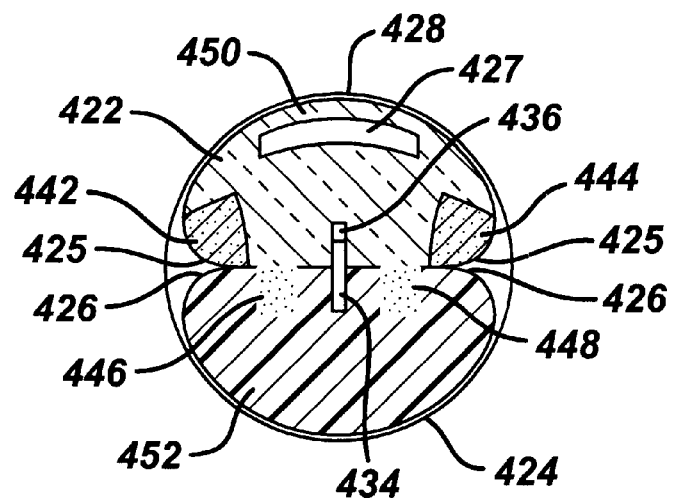
FIG. 37 is a cross sectional view of the jaws (FIG. 32) of an electrosurgical instrument having a feedback light in accordance with the present invention.
Figure 38:
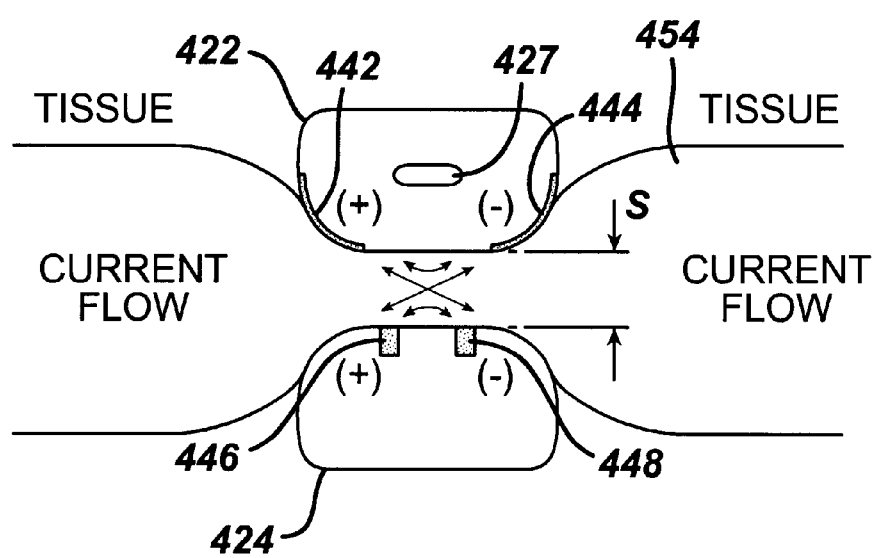
FIG. 38 is a cross-sectional view of the jaws of the electrosurgical instrument having a feedback light, with uncoagulated tissue disposed therebetween, showing the path of current flow between the two jaw members.

FIG. 37 further illustrates feedback light 427 housed within first moveable jaw 422, however other embodiment of the present invention may include feedback light 427 housed within second moveable jaw 424, feedback light 427 housed within first and second moveable jaws 422, 424, and feedback light 427 affixed externally to one or both of first and second moveable jaws 422, 424. The distal placement of feedback light 427, in close proximity to the area of surgical application, provides the operator with a clear indicator of when tissue 454 has been sufficiently desiccated to insure proper hemostasis while reducing lateral damage due to over exposure of electric current.

Figure 35:
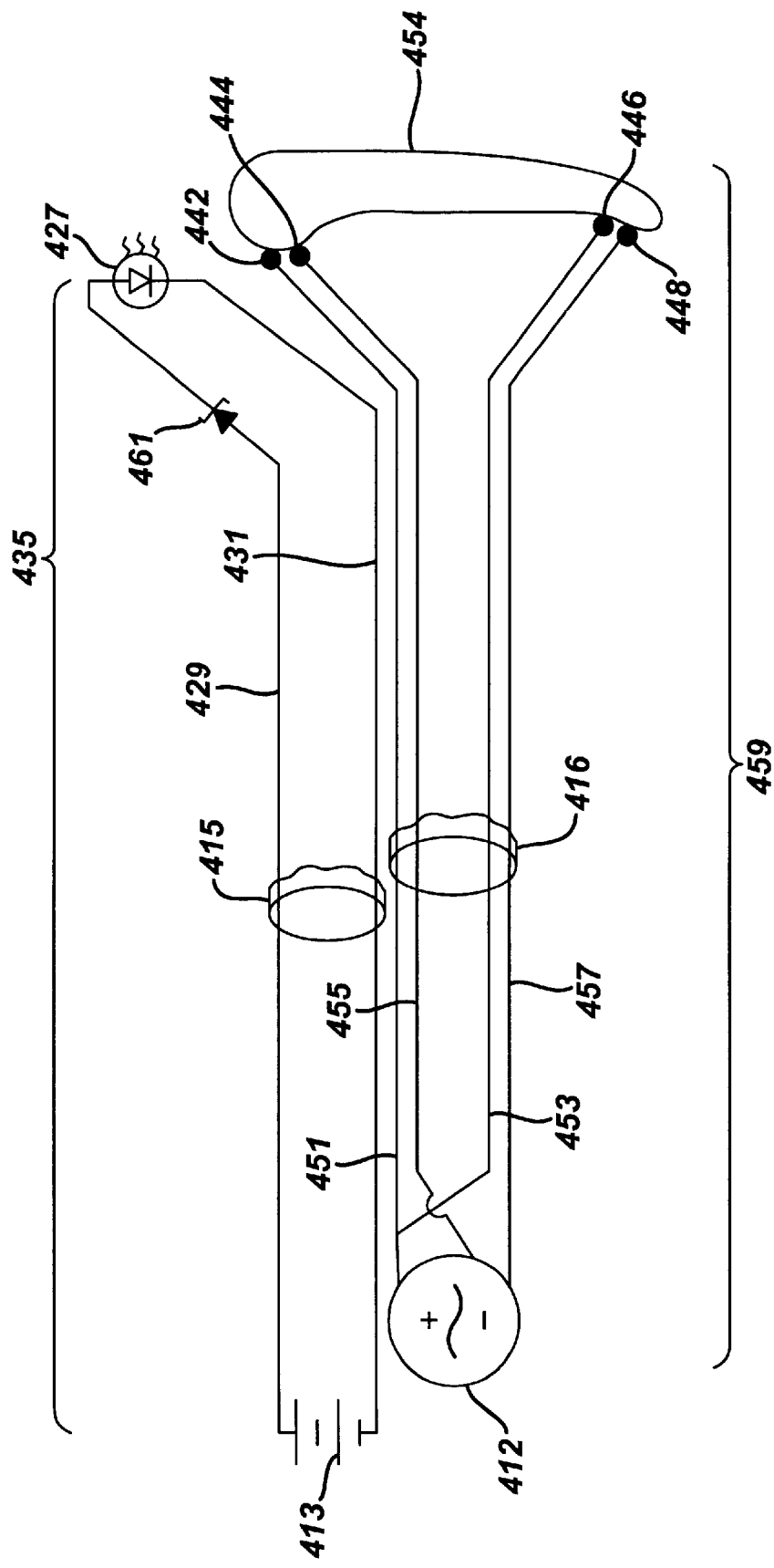
FIG. 35 illustrates an electrical schematic of an alternate embodiment of an electrosurgical instrument having a feedback light in accordance with the present invention.

FIG. 35 illustrates a further embodiment of the present invention. First lead 429 includes a Zener diode 461 that functions to transfer current through untwisted circuit 435 only after a specific voltage threshold has been exceeded. This feature allows, for example, the operator to set the voltage threshold of the Zener diode 461 just above the voltage of battery 413 allowing feedback light 427 to light only when capacitively coupled voltage from untwisted transmission circuit 459 is present. The operator will be able to carefully tune the electrosurgical instrument system 410 to his exact needs by selecting the appropriate battery 413 voltage, feedback light 427 voltage, and the Zener diode 416 threshold voltage, providing a highly controlled qualitative indicator of the power passing through the instrument. When tissue 454 desiccates, it will increase the impedance of the untwisted transmission circuit 459 resulting in a loss of current transmitted by capacitive coupling, causing the feedback light 427 to dim or turn off. Dimming, or inactivity of feedback light 427 signals the operator to cease applying electrosurgical current to a tissue 454 in order to prevent burns or lateral tissue damage.

Figure 36:
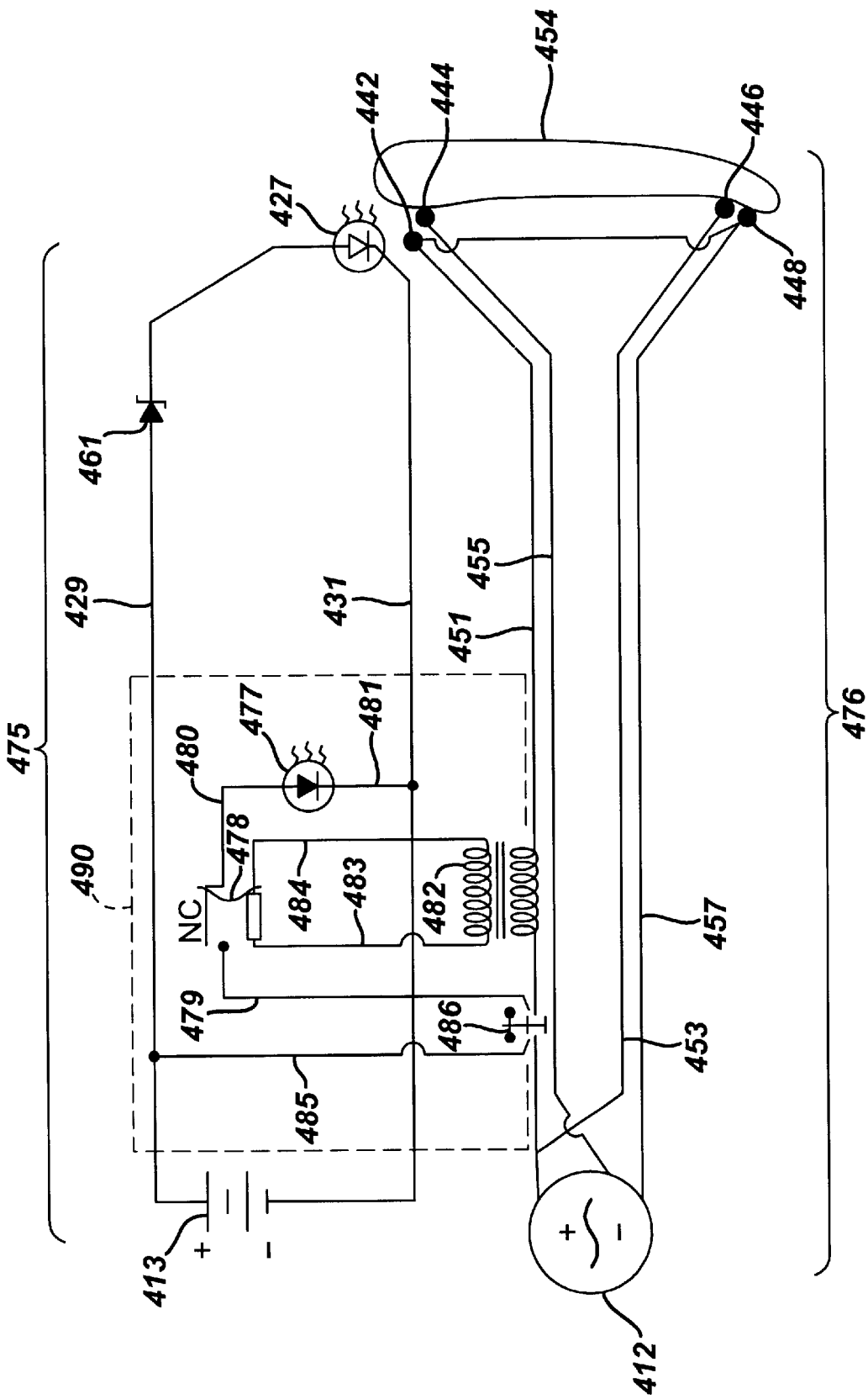
FIG. 36 illustrates an electrical schematic of an alternate embodiment of an electrosurgical instrument having a feedback light in accordance with the present invention.

FIG. 36 illustrates an electrical schematic of a further embodiment of the present invention. FIG. 36 further discloses a second feedback light 477, a relay 478, leads 485, 479, 480, 481, 483, 484, transformer 482, and switch 486, herein collectively known as feedback means 490. Feedback means 490 functions to detect when a first level of impedance of tissue 454 has been exceeded. Depression of switch 486 completes the coupled transmission circuit 476 allowing energy to flow through tissue 454. Depression of switch 486 further couples lead 485 to lead 479. Lead 479 is coupled to relay 478. Relay 478 is normally closed when electric current is not running through leads 483, 484. When switch 486 is depressed and electrical current passes through coupled transmission circuit 476, energy is transmitted through leads 483, 484 due to inductive coupling via transformer 482. Current passing through leads 483, 484 causes relay 478 to open breaking the circuit connecting lead 479 to lead 480, second feedback light 477, and lead 481. When decreased electric current is not passing through coupled transmission circuit 476, as when switch 486 has not been depressed or when impedance has significantly decreased the voltage of coupled transmission circuit 476, relay 478 will be closed due to a lack of significant inductive coupling in transformer 482. When relay 478 is closed, DC current originating from battery 413 passes through leads 485, 479, relay 478, lead 480, second feedback light 477, and leads 481, 431, where this current functions to light second feedback light 477.

The lighting of second feedback light 477 alerts the operator that significant electric current is not passing through coupled transmission circuit 476 and that either the instrument is not active or that tissue 454 has been appropriately desiccated. Significant current passing through transmission circuit 476 is inductively coupled through transformer 482 to relay 478, where the presence of current then lights first feedback light 427. The opening of relay 478 extinguishes second feedback light 477, alerting the operator that a significant electric current is passing through coupled transmission circuit 476. This embodiment of the present invention functions to light feedback light 427 when coupled transmission circuit 476 carries a significant voltage and extinguishes feedback light 427 when coupled transmission circuit 427 no longer carries a significant electric current. At the same time, a lack of significant current in coupled transmission circuit 476 will cause second feedback light 477 to light.

The use of a second light provides the operator with an extra measure of security in determining when a significant level of voltage is no longer passing through coupled transmission circuit 476 due to impedance caused by the desiccation of tissue 454. A significant level of electrical current refers to the voltage requirements or outputs of the feedback lights, Zener diodes, batteries, or other electrical components designed to provide the operator with the level of qualitative feedback for a particular application. Dimming, or inactivity of feedback light 427 and the lighting of second feedback light 477 signals the operator to cease applying electrosurgical current to a tissue 454 in order to prevent burns or lateral tissue damage. The present invention further may also include the use of a plurality of feedback lights, a plurality of relays, a plurality of transformers, twisted or untwisted leads, a plurality of switches, and or the use of capacitive and/or inductive coupling. It will be clear to one of ordinary skill in the art that a number of electrical configurations to achieve the desired qualitative feedback result are possible.

Figure 39:
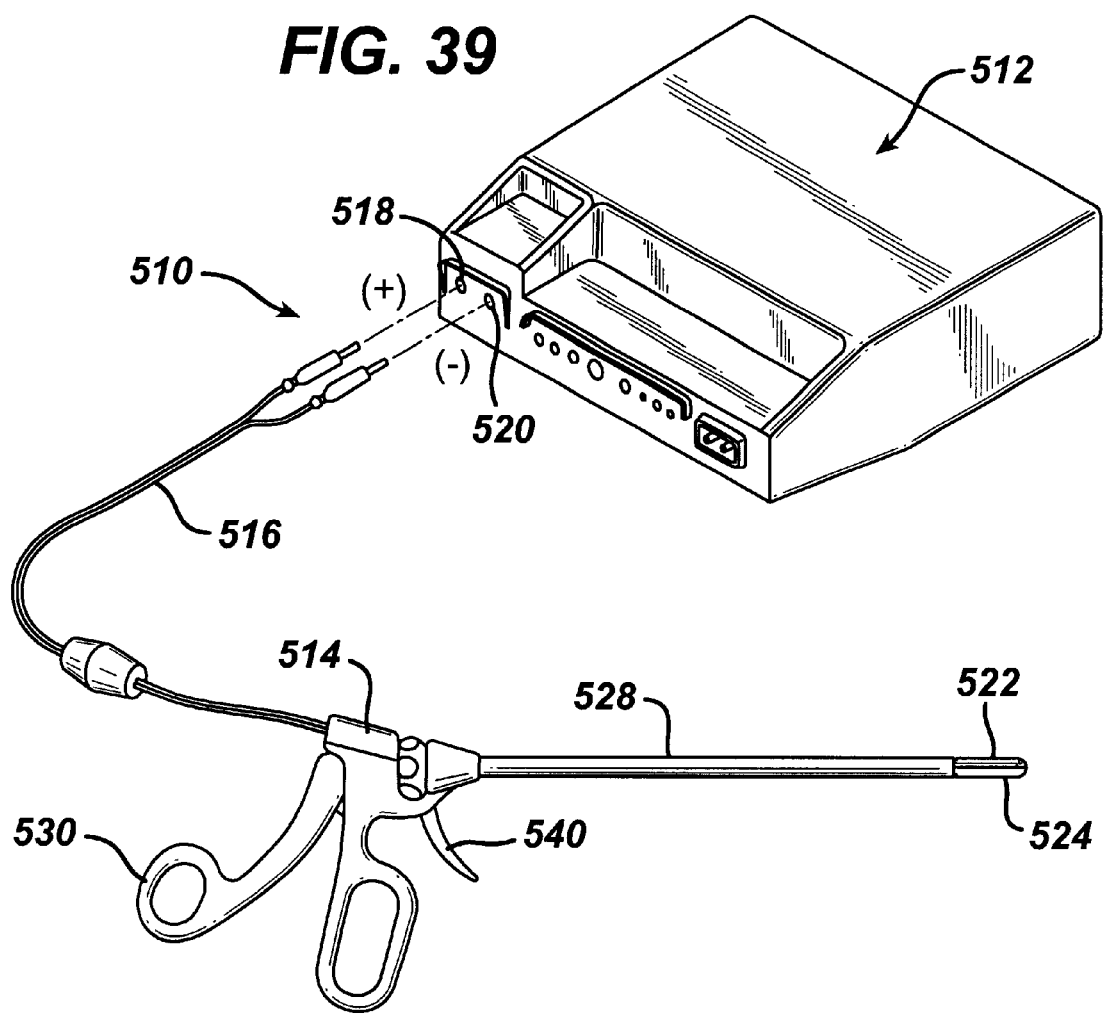
FIG. 39 is a perspective view of an electrosurgical instrument in accordance with the present invention shown with an associated electrosurgical current generating unit and connector cable.

FIG. 39 illustrates a perspective view of an electrosurgical instrument system, generally designated 510, embodying the present invention. The illustrated system includes an RF energy generator 512, a housing 514, and a cable 516 that connects the housing 514 to the positive bipolar output plug clip receptacle 518, and negative bipolar output plug clip receptacle 520 of the generator 512, where the housing is adapted to transmit electric current to electrode 542 housed within first moveable jaw 522 and to electrode 546 housed within second moveable jaw 524. First moveable jaw 522 further houses guard electrodes 550, 560 and second moveable jaw 524 further houses guard electrodes 570, 580, wherein guard electrodes 550, 560, 570, 580 may be connected to a grounding pad (not shown). While the illustrated first and second moveable jaws 522, 524 are endoscopic jaws for use in minimally invasive surgical procedures, the invention of the present application is equally applicable to jaws designed for use in open surgical procedures.

The illustrated RF generator 512 may be, for example, a unitary monopolar-bipolar RF generator, such as the PEGASYS RF generator, and thus also include plug clip receptacles for the monopolar active and return terminals. However, for the purposes of the present invention, only the bipolar current generating feature is utilized.

Figure 40:
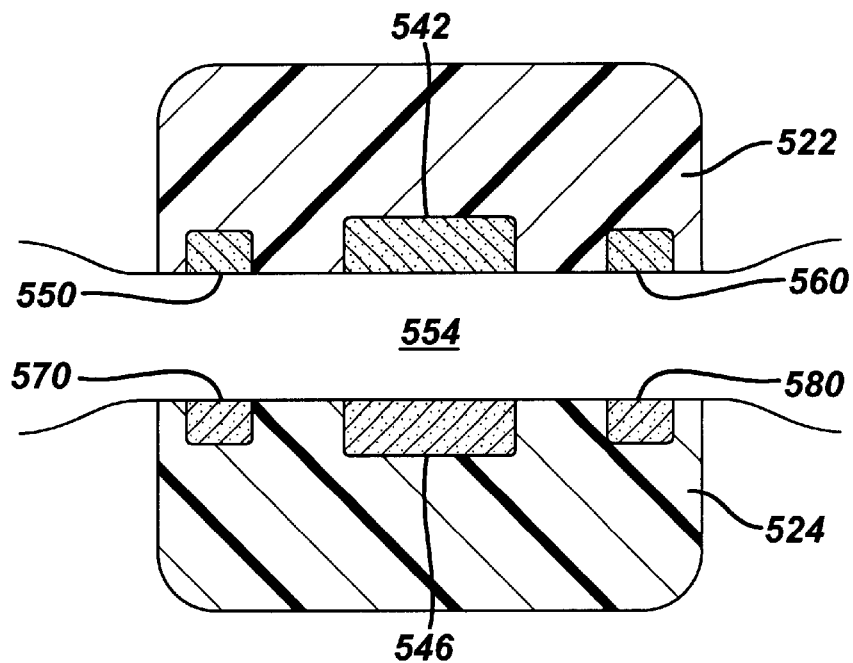
FIG. 40 is a cross sectional view of the jaws of an electrosurgical instrument having a plurality of guard electrodes in accordance with the present invention.

FIG. 40 illustrates a cross section of one embodiment of the present invention comprising first moveable jaw 522 having electrode 542 and guard electrodes 550, 560 and second moveable jaw 524 having electrode 546 and guard electrodes 570, 580. When first and second moveable jaws are clamped onto tissue 554 and electrodes 542, 546 are electrically activated via generator 512, electric current is passed through tissue 554, where the electric current desiccates tissue 554. As tissue 554 desiccates, the impedance of tissue 554 rises. As the impedance of tissue 554 rises between electrode 542 and electrode 546 the electric current may choose a path of lesser resistance from electrode 542 to guard electrodes 550, 560, 570, 580 or from electrode 546 to guard electrodes 550, 560, 570, 580. Attraction of electric current to guard electrodes 550, 560, 570, 580 when tissue impedance is high between electrode 542 and electrode 546 will contain lateral electric current and will prevent electric current from causing serious lateral tissue damage. In order for guard electrodes 550, 560, 570, 580 to be a favorable transmission surface, they may be held at a desirable charge potential actively such as, for example, by incorporating resistors connecting guard electrodes 550, 560, 570, 580 to generator 512; a grounding pad connected to ground electrodes 550, 560, 570, 580; or by using sense electrodes in cooperation with guard electrodes that transmit the presence of lateral current flow to the generator, where this functions to decrease generator 512 output and/or warn the operator of the presence of lateral electric current flow. Guard electrodes may also operate in a passive system such as, for example, where guard electrodes 550, 560, 570, 580 form an autonomous unit. The present invention may also include the use of other configurations of guard electrodes 550, 560, 570, 580 and/or sense electrodes (not shown) that substantially achieve the function of reducing thermal damage to tissue outside the desired cutting/coagulating region. The present invention may also include a plurality of guard electrodes 550, 560, 570, 580, and/or sense electrodes, a combination of features of the disclosed embodiments such as, for example, resistors used in cooperation with sense electrodes, and the use of other electrical features not disclosed that would be apparent to one skilled in the art to achieve the desired function.

Figure 41:
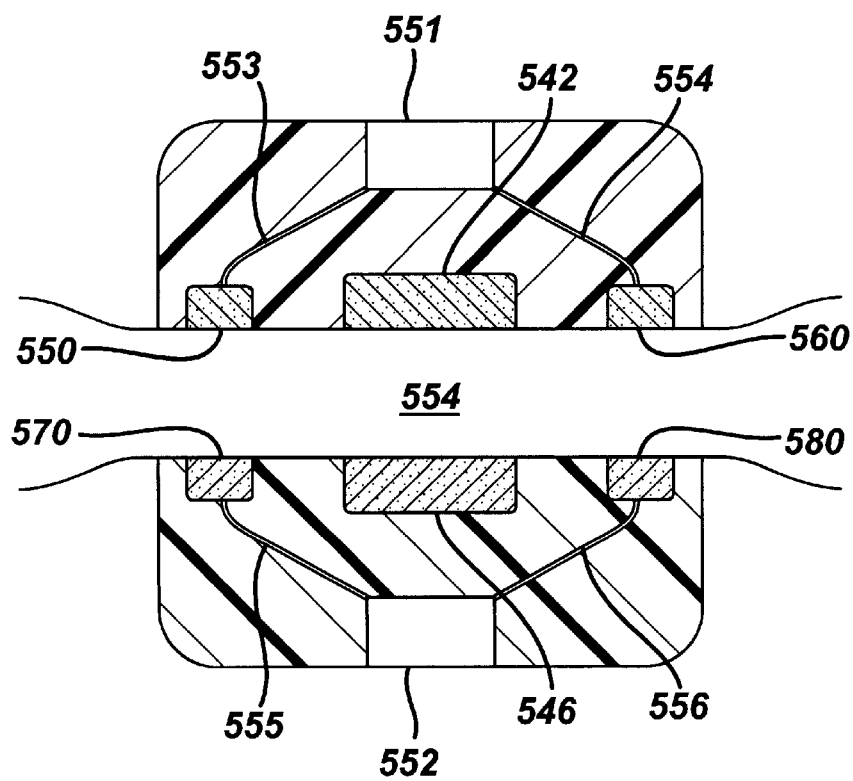
FIG. 41 is a cross sectional view of the jaws of an electrosurgical instrument having a plurality of electrodes and a feedback device in accordance with the present invention.

FIG. 41 illustrates a further embodiment of the present invention comprising guard electrodes 550, 560, 570, 580, connected to feedback lights 551, 552, via leads 553, 554, 555, 556, where feedback lights 551, 552 will light if lateral current is picked up by guard electrodes 550, 560, 570, 580. The presence of feedback light 551, 522 will indicate to an operator when the impedance of tissue 554 has increased substantially as to favor the transmission of electric current of guard electrodes 550, 560, 570, 580, where the feedback light will indicate to the operator that undesirable lateral current flow is occurring. The present invention may also include the use of a single feedback light 551, or a plurality of feedback lights. The feedback light is located preferably in the distal portion of the end effector in order to provide direct visual feedback to the operator in the area of operation, however the feedback light 551 may be located anywhere on the instrument or external to the instrument desirable for a surgical procedure. Feedback light 551 may be any feedback device such as an light emitting diode (LED), an audio alarm, a generator shut down system, or other suitable feedback device. The feedback device may be directly coupled, inductively coupled, or capacitively coupled to one or a plurality of feedback electrodes, ground electrodes, and/or sense electrodes.

Figure 42:
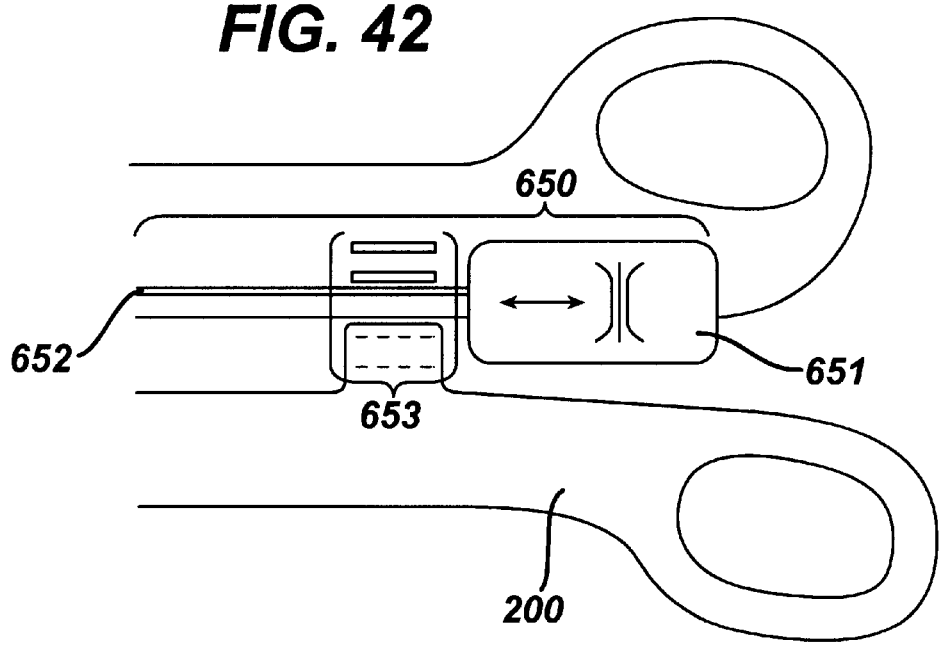
FIG. 42 is a partial view of an electrosurgical instrument in accordance with the present invention having a knife lock out system.

FIG. 42 illustrates a further embodiment of the present invention comprising a knife lock out system 650 for hemostat 200, where lock out system 650 may also include a knife actuator 651, such as a slide switch. Knife actuator 651 is connected to a knife rod 652, and a ratchet 653. The distal end of knife rod 652 is affixed to sliding knife 220 and the proximal end of knife rod 652 is affixed to knife actuator 651. When hemostat 200 is in a closed position, knife actuator 651 may be actuated, extending the sliding knife 220. As sliding knife 220 is extended distally, knife actuator 651 engages closed ratchet 653 effectively locking hemostat 200 in the closed position. Hemostat 200 may only open after knife actuator 651 retracts from its engagement with ratchet 653. Knife finger actuator 651 may hold ratchet 653 when engaged with ratchet 653 by engaging male protrusions of the ratchet 653 with corresponding female groves of the knife actuator 651, however other suitable means of engagement between ratchet 653 and knife actuator 651 are consistent with the present invention. Engaging knife actuator 651 with ratchet 653 while sliding knife 220 is extended prevents the operator from opening the blade and continuing the application in a knife-exposed mode. This safety prevents the operator from opening the hemostat until the sliding knife 220 is retracted.

Figure 43:
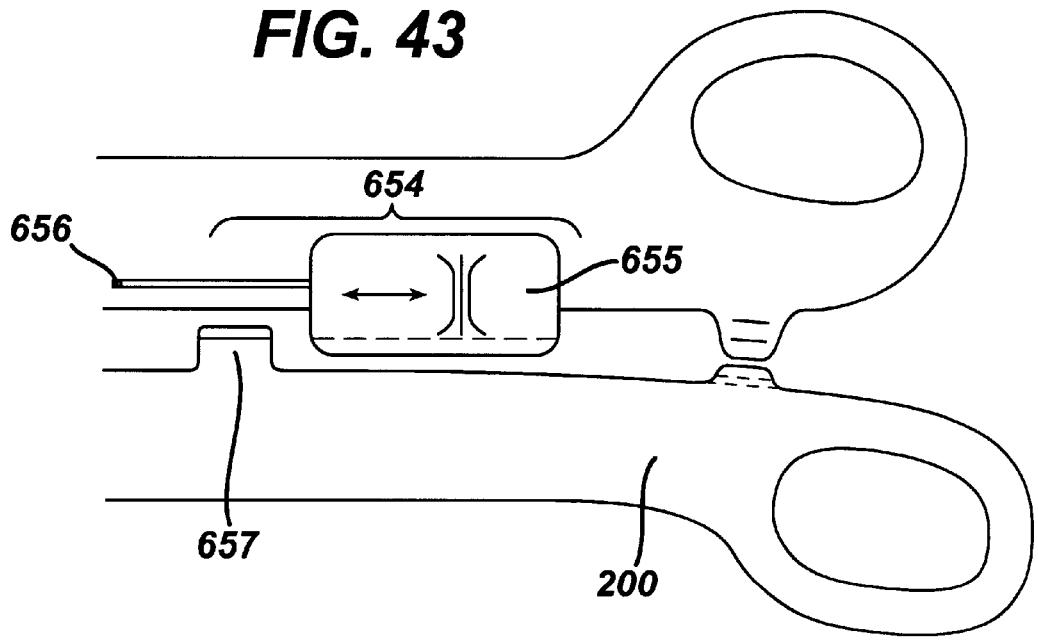
FIG. 43 is a partial view of an electrosurgical instrument in accordance with the present invention having a knife lock out system.

FIG. 43 illustrates a further embodiment of the present invention comprising an alternate knife lock out system 654 having a knife lock out latch 657. Male protrusions of the knife lock out latch 657 correspond with female groves of the knife actuator 655, however other suitable means of engagement between knife lock out latch 657 and knife finger actuator 655 are consistent with the present invention.

Figure 44:
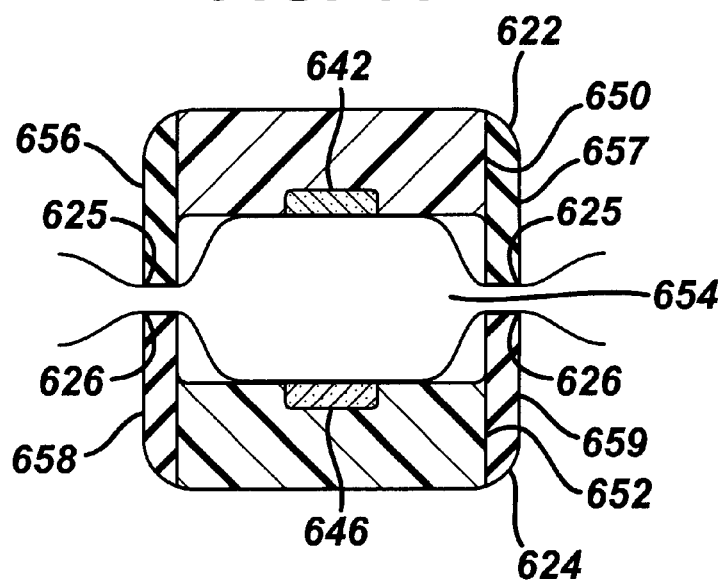
FIG. 44 is a section view of an alternate embodiment of a first and second moveable jaws comprising a tissue contacting surface in accordance with the present invention.

FIG. 44, In keeping with the present invention, illustrates first and second moveable jaws 622, 624 comprising a first tissue contacting surface 625 and a second tissue contacting surface 626 including a first insulating member 650 and a second insulating member 652, respectively, where first and second insulating members 650, 652 are made from an insulative material such as plastic, rubber, NYLON, polytetraflouroethylene (PTFE), or other suitable insulative material. First moveable jaw 622 includes a first electrode 642. Second moveable jaw 624 includes a second electrode 646. The first and second tissue contacting surfaces 625, 626 of the first and second moveable jaws 622, 624 are in a generally face-to-face relationship, with the first electrode 642 associated with first moveable jaw 622 is in face-to-face relationship with the corresponding first electrode 646 of second moveable jaw 624. First moveable jaw 622 further may also include a first dam member 656 and a second dam member 657. Second moveable jaw 624 may also include a first dam member 658 and a second dam member 659, where first dam member 656 and first dam member 658 are opposable, and second dam member 657 and second dam member 659 are opposable. When first electrode 642 and first electrode 646 are electrically activated, tissue 654 held between first dam members 656, 658 and tissue 654 held between second dam members 657, 659 will have a high impedance due to the pressure applied by first dam members 656, 658 and second dam members 657, 659. An increase in tissue impedance in the regions adjacent first dam members 656, 658 and second dam members 657, 659 will discourage the transmission of electric current though the region of high tissue impedance, inhibiting the transmission of electric current outside of first moveable jaw 622 and second moveable jaw 624, whereby decreasing the risk of unwanted lateral tissue damage. First dam members 656, 658 and second dam members 657, 659 may be extended from first moveable jaw 622 and second moveable jaw 624 from 0.0005 inches–0.015 inches respectively, however other suitable measurements desirable for a particular application are consistent with the present invention.

The present invention may also include the use of first dam member 656 and second dam member 657 of first moveable jaw 622 to be used in the absence of first dam member 658 and second dam member 659 of second moveable jaw 624. The present invention may also include the use of first dam member 658 and second dam member 659 in the absence of first dam member 656 and second dam member 657 of first moveable jaw 622. First dam members 656, 658 and second dam members 657, 659 may be any shape suitable for use in a surgical application such as an interlocking form, where, for example, a male portion of first dam member 656 and second dam member 657 fit into corresponding female portions of first dam member 658 and second dam member 659, respectively, a flat surfaced embodiment where the faces of first dam members 656, 658 and second dam members 657 and 659 are substantially flush with one another, or other forms suitable for use with a surgical procedure. First and second electrodes 642, 646 may be electrically activated by a connection to a generator 312 via a cable 316 or by other suitable electrically activating means. First dam members 656, 658 and second dam members 657, 659 may be permanently affixed, or removably detachable from first moveable jaw 622 and second moveable jaw 624, respectively. For purposes herein, first dam members 656, 658 and second dam members 657, 659 may be collectively called a tissue dam.

Figure 45:
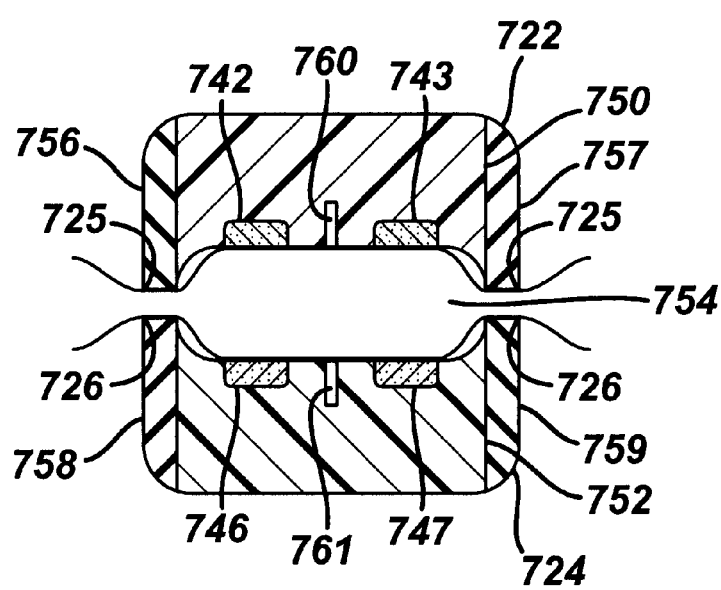
FIG. 45 is a section view of an alternate embodiment of a first and second moveable jaws comprising a tissue contacting surface in accordance with the present invention.
Figure 45A:
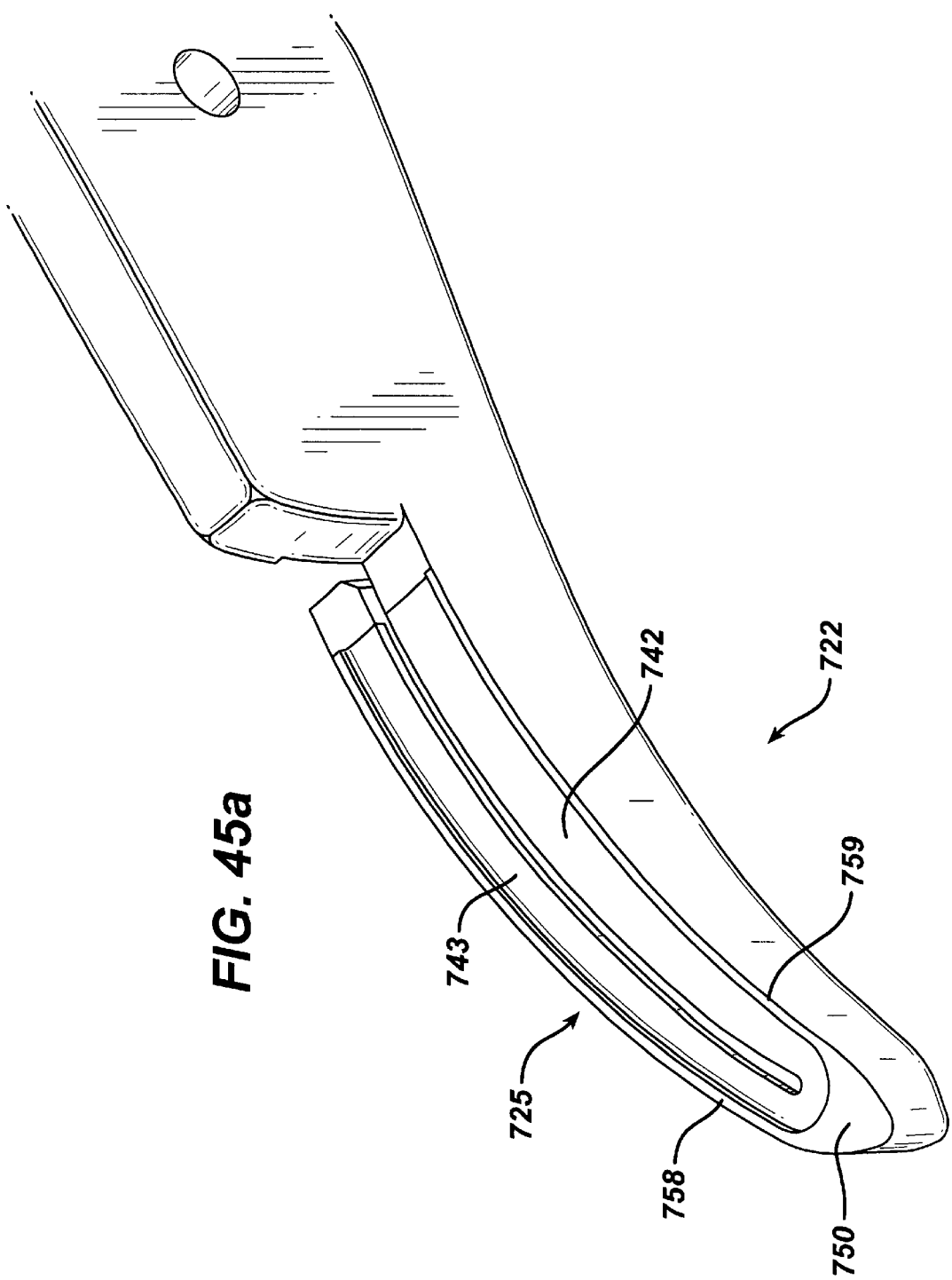
FIG. 45a is a perspective view of an alternate embodiment of a first and second moveable jaws comprising a tissue contacting surface in accordance with the present invention.

FIGS. 45 and 45a illustrate first and second moveable jaws 722, 724, the features of the illustrated embodiment corresponding to like features and attributes of the embodiment shown in FIG. 44, but referenced with "700" series reference numerals for similar features. Jaws 722 and 724 comprise a first tissue contacting surface 725 and a second tissue contacting surface 726 including a first insulating member 750 and a second insulating member 752, respectively, where first and second insulating members 750, 752 are made from an insulative material such as plastic, rubber, NYLON, polytetraflouroethylene (PTFE), or other suitable insulative material. First moveable jaw 722 includes a first electrode 742 and a second electrode 743. Second moveable jaw 724 includes a first electrode 746 and a second electrode 747. The first and second tissue contacting surfaces 725, 726 of the first and second moveable jaws 722, 724 are in a generally face-to-face relationship, where the first electrode 742 and second electrode 743 associated with first moveable jaw 622 are in face-to-face relationship with the corresponding first electrode 746 and second electrode 747 of second moveable jaw 724. First moveable jaw 722 further may also include a first dam member 756 and a second dam member 757. Second moveable jaw 724 may also include a first dam member 758 and a second dam member 759, where first dam member 756 and first dam member 758 are opposable, and second dam member 757 and second dam member 759 are opposable. When first electrode 742 and second electrode 743 of first moveable jaw 722 and first electrode 746 and second electrode 747 of second moveable jaw 724 are electrically activated, tissue 754 held between first dam members 756, 758 and tissue 754 held between second dam members 757, 759 will have a high impedance due to the pressure applied by first dam members 756, 758 and second dam members 757, 759. An increase in tissue impedance in the regions adjacent first dam members 756, 758 and second dam members 757, 759 will discourage the transmission of electric current though the region of high tissue impedance, inhibiting the transmission of electric current outside of first moveable jaw 722 and second moveable jaw 724, whereby decreasing the risk of unwanted lateral tissue damage.

Figure 46:
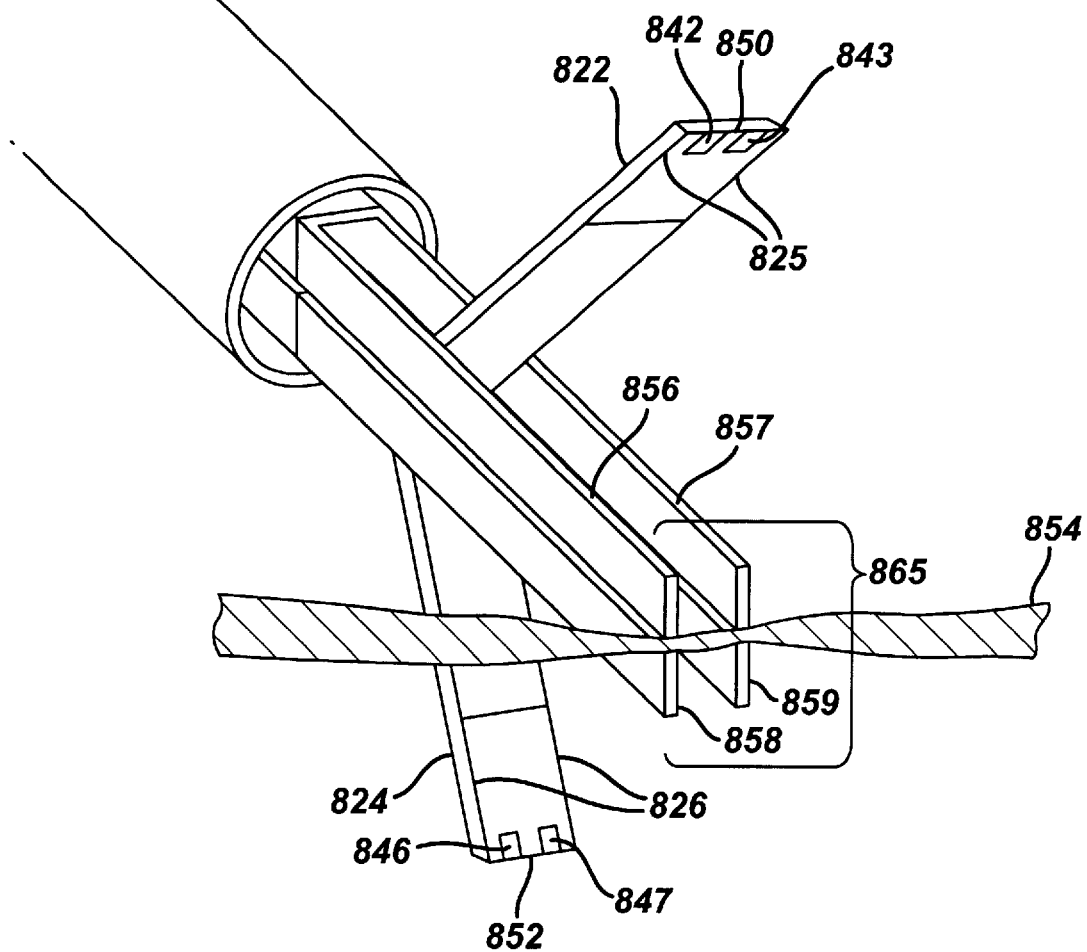
FIG. 46 is a perspective view of an alternate embodiment of a first and second moveable jaws comprising a tissue contacting surface in accordance with the present invention.

FIG. 46 illustrates a further embodiment of the present invention comprising first and second moveable jaws 822, 824 comprising a first tissue contacting surface 825 and a second tissue contacting surface 826 including a first insulating member 850 and a second insulating member 852, respectively, where first and second insulating members 850, 852 are made from an insulative material such as plastic, rubber, polytetraflouroethylene (PTFE), or other suitable insulative material. First moveable jaw 822 includes a first electrode 842 and a second electrode 843. Second moveable jaw 824 includes a first electrode 846 and a second electrode 847. The first and second tissue contacting surfaces 825, 826 of the first and second moveable jaws 822, 824 are in a generally face-to-face relationship, where the first electrode 842 and second electrode 843 associated with first moveable jaw 822 are in face-to-face relationship with the corresponding first electrode 846 and second electrode 847 of second moveable jaw 824. One embodiment of the present invention further may also include a first dam member 856 and a second dam member 857 a first dam member 858 and a second dam member 859, where first dam member 856 and first dam member 858 are opposable, and second dam member 857 and second dam member 859 are opposable. For purposes herein, first dam members 856, 858 and second dam members 857, 858 may be collectively called an independent tissue dam 865. When first electrode 842 and second electrode 843 of first moveable jaw 822 and first electrode 846 and second electrode 847 of second moveable jaw 824 are electrically activated, tissue 854 held between first dam members 856, 858 and tissue 854 held between second dam members 857, 859 will have a high impedance due to the pressure applied by first dam members 856, 858 and second dam members 857, 859.

The illustrated embodiment allows the operator to apply pressure to the first dam members 856, 858 and second dam members 857, 859 independently of the pressure applied from first moveable jaw 822 and second moveable jaw 824. The ability to apply controlled pressure with both the independent tissue dam 865 and first and second moveable jaws 822, 824 allows for greater manipulation and control of an area to be cut and/or coagulated during a procedure. An increase in tissue impedance in the regions adjacent first dam members 856, 858 and second dam members 857, 859 will discourage the transmission of electric current though the region of high tissue impedance, inhibiting the transmission of electric current outside of first moveable jaw 822 and second moveable jaw 824, whereby decreasing the risk of unwanted lateral tissue damage.

The present invention may also include the use of first dam member 856 and second dam member 857 in the absence of first dam member 858 and second dam member 859. Independent tissue dam 865 may be actuated by a trigger mechanism, a scissors mechanism, or by other means of actuation known in the art. First moveable jaw 822 and second moveable jaw 824 may be actuated independently of independent tissue dam 865 by a camming system, a scissors system, or by other means of actuation commonly known in the art. First dam members 856, 858 and second dam members 857, 859 may be any shape suitable for use in a surgical application such as an interlocking form, where, for example, a male portion of first dam member 856 and second dam member 857 fit into corresponding female portions of first dam member 858 and second dam member 859, respectively, a flat surfaced embodiment where the faces of first dam members 856, 858 and second dam members 857 and 858 are substantially flush with one another, or other forms suitable for use with a surgical procedure. First electrodes 842, 846 and second electrodes 843, 847 may be electrically activated by a connection to a generator 312 via a cable 316 or by other suitable electrically activating means. One embodiment of the present invention may also include the disposal, after one use, of the tissue dam and/or the entire instrument (not shown). A further embodiment of the present invention may also include the use of a sliding knife 220 that may be actuated through knife slots (not shown). The present invention may also include the use a feedback system, such as, a light emitting diode as previously described herein, to indicate, for example, lateral thermal spread, impedance levels, or other variables, a single pair of electrodes, a plurality of electrodes, removable first and second moveable jaws 822, 824 from Independent tissue dam 865, where independent tissue dam 865 would function as a hemostat, a plurality of first dam members 856, 858 and/or second dam members 857, 859, tissue cutting elements not having opposable jaws, tissue cutting elements utilizing energy sources other than RF electrosurgical energy such as, for example, ultrasound or laser.

Figure 47:
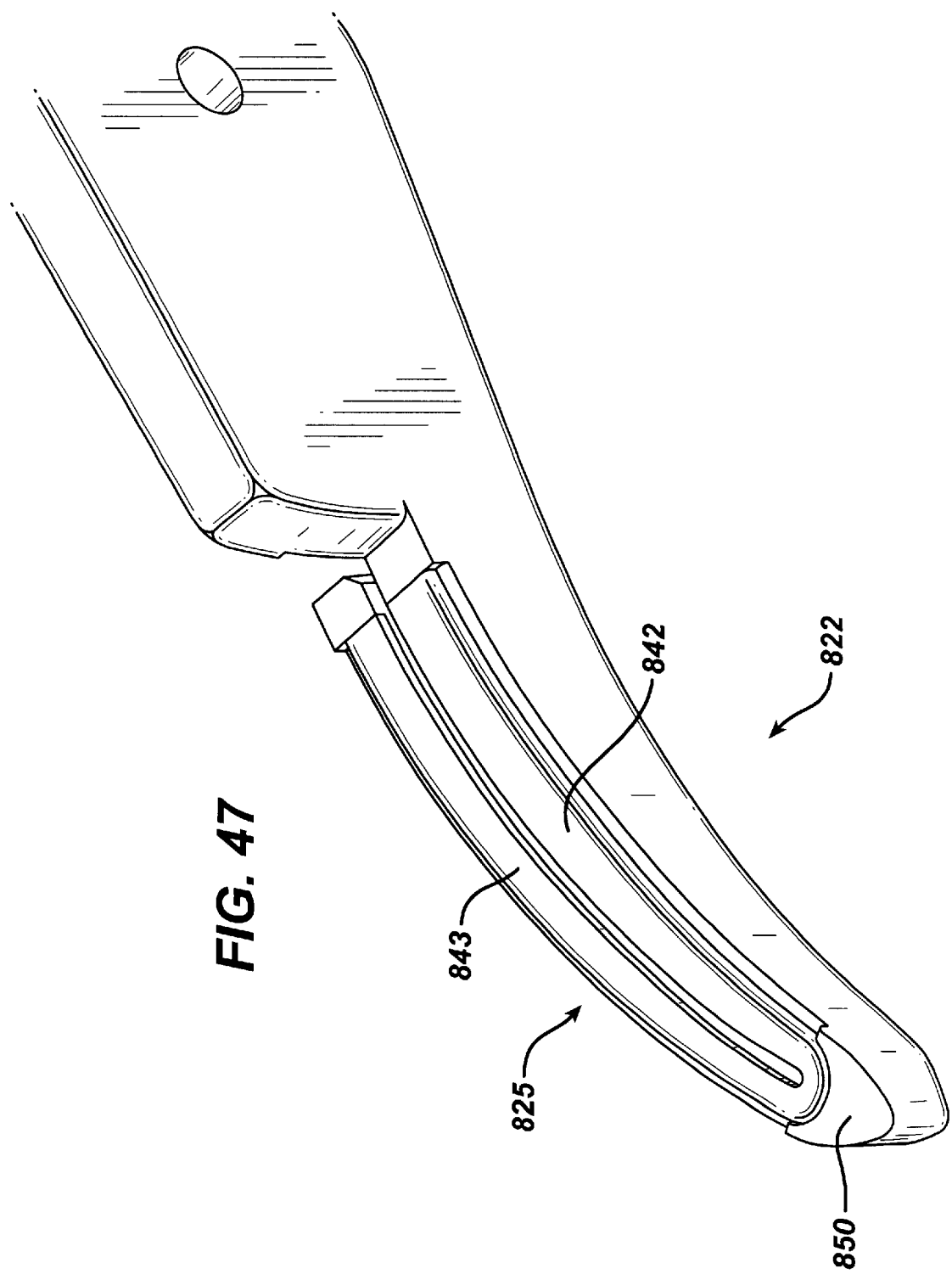
FIG. 47 is a perspective view of a jaw in accordance with the present invention, wherein the tissue dam is located at the distal end of the jaw.
Figure 48:
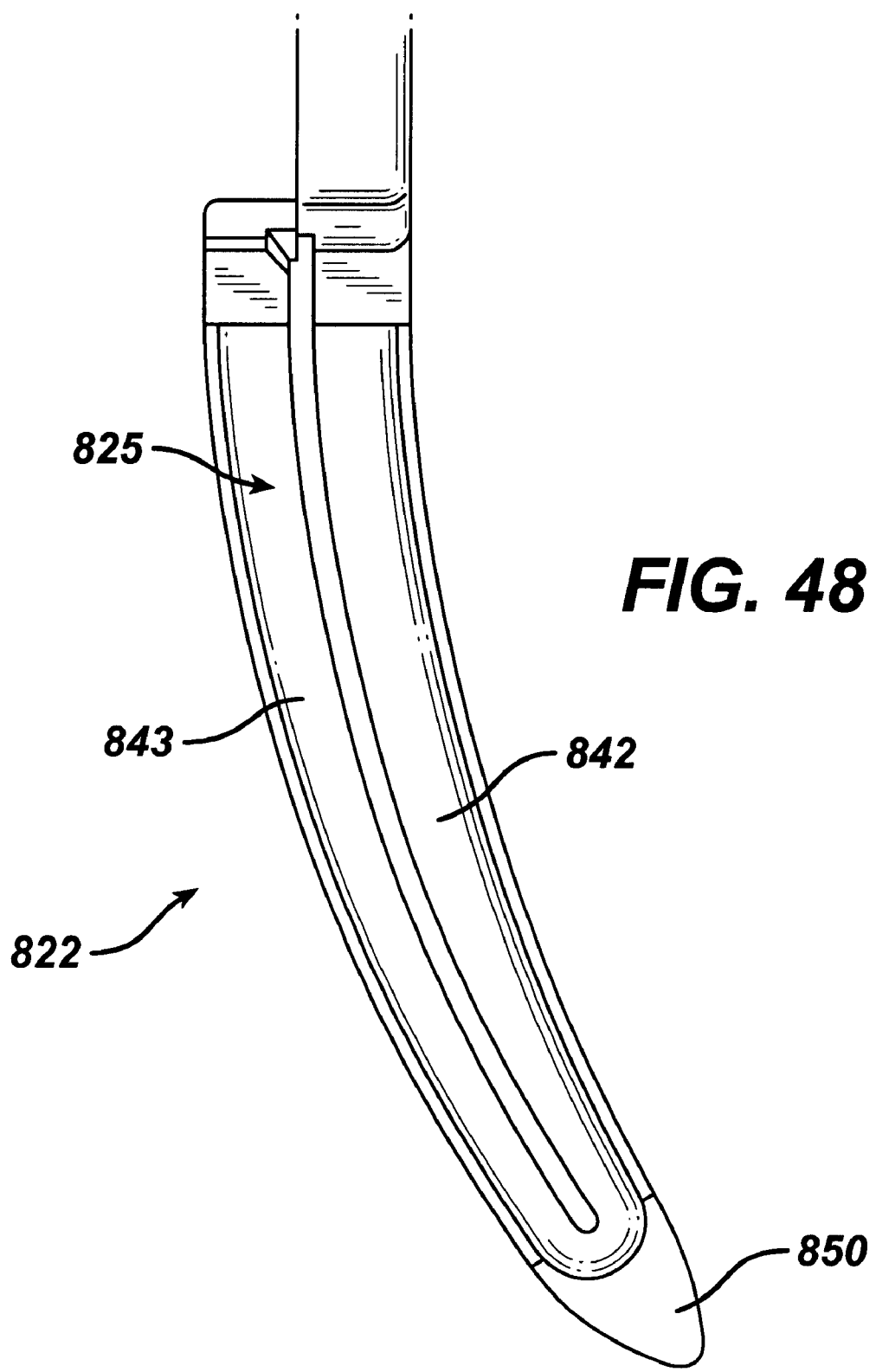
FIG. 48 is a top view of the jaw illustrated in FIG. 47.

FIGS. 47 through 49 illustrate an embodiment of the present invention wherein first moveable jaw 822 may also include a first tissue contacting surface 825 including a first insulating member 850 where insulating member 850 is made from an insulative material such as plastic, rubber, nylon polytetraflouroethylene (PTFE), or other suitable insulative material. First moveable jaw 822 includes a first electrode 842 and a second electrode 843. In this embodiment, first insulating member 850 acts as a tissue dam at the distal end of first movable jaw 822. First insulating member 850 is raised above first electrode 842 only at the distal end of first movable jaw 822. Insulating members such as, for example, first insulating member 850 may alternately be coatings that may be sprayed onto first movable jaw 822, or by using alternate coating methods such as, for example, dipping, plasma coating, encasement, or the like.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, as would be apparent to those skilled in the art, the disclosures herein of the electrode configuration, including the cutting knife used as either means for coagulation, and mechanical grasping and cutting as well as the tissue dam and indicator light have equal application in robotic-assisted surgery. In addition, it should be understood that every structure described above has a function and such structure can be referred to as a means for performing that function. Accordingly, it is intended that the invention be limited only by the spirit and scope of the appended claims.

What is claimed is:

1. An electrosurgical apparatus comprising:
    first and second moveable jaws, each jaw including a tissue contacting surface in face-to-face relation with the tissue contacting surface of the other jaw;
    said grasping jaws being relatively movable for grasping tissue between said tissue contacting surfaces;
    said tissue contacting surfaces of said jaws comprising an insulating material;
    a first and second electrode housed within said first moveable jaw and said second moveable jaw, respectively, wherein said first and second electrodes are connectable to a first circuit for providing an electrical current between said first and second electrodes; and
    a feedback light, wherein said feedback light is positioned on said first moveable jaw, wherein said feedback light is connectable to a first lead and a second lead, whereby forming a second circuit, wherein said second circuit is adjacent to said first circuit, whereby facilitating capacitive coupling between said first circuit and said second circuit, whereby lighting said feedback light.

2. Apparatus of claim 1, wherein said feedback light is an LED.

3. The apparatus of claim 1, further comprising a biased power source, wherein said biased power source is coupled to said second circuit, wherein said biased power source delivers direct current through said second circuit.

4. The apparatus of claim 3, further comprising a first Zener diode, wherein said first Zener diode is positioned on said second circuit, wherein said first Zener diode has an established voltage threshold.

5. The apparatus of claim 4, further comprising a second Zener diode, wherein said second Zener diode is positioned on said second circuit.

6. The apparatus of claim 1, further comprising a feedback means for indicating when a first level of impedance has been reached.

7. An electrosurgical apparatus comprising:
    first and second moveable jaws, each jaw including a tissue contacting surface in face-to-face relation with the tissue contacting surface of the other jaw;
    said grasping jaws-being-relatively movable for grasping tissue between said tissue contacting surfaces;
    said tissue contacting surfaces of said jaws comprising an insulating material;
    a first and second electrode housed within said first moveable jaw and said second moveable jaw, respectively, wherein said first and second electrodes are connectable to a first circuit for providing an electrical current between said first and second electrodes; and
    a feedback light, wherein said feedback light is positioned on said first moveable jaw, wherein said feedback light is connectable to a first lead, a second lead, and a toroid, wherein said second lead is wound around said toroid, whereby forming a second circuit, wherein a third lead of said first circuit passes through said toroid, whereby facilitating inductive coupling between said first circuit and said second circuit, whereby lighting said feedback light.

8. The apparatus of claim 7, wherein said insulating material of said tissue contacting surface comprises a transparent material.

9. The apparatus of claim 8, wherein said insulating material houses said feedback light.

10. The apparatus of claim 7, further comprising a first Zener diode, wherein said first Zener diode is positioned along said second circuit.

11. The apparatus of claim 10, further comprising a second Zener diode, wherein said second Zener diode is positioned along said second circuit.

12. The apparatus of claim 10, wherein said first Zener diode is electrically biased by a battery.

* * * * *